US008512718B2

(12) United States Patent
Eini et al.

(10) Patent No.: US 8,512,718 B2
(45) Date of Patent: *Aug. 20, 2013

(54) PHARMACEUTICAL COMPOSITION FOR TOPICAL APPLICATION

(75) Inventors: Meir Eini, Ness Ziona (IL); Dov Tamarkin, Maccabim (IL)

(73) Assignee: Foamix Ltd., Rehovot (IL)

(*) Notice: Subject to any disclaimer, the term of this patent is extended or adjusted under 35 U.S.C. 154(b) by 229 days.

This patent is subject to a terminal disclaimer.

(21) Appl. No.: 12/705,219

(22) Filed: Feb. 12, 2010

(65) Prior Publication Data

US 2010/0137198 A1 Jun. 3, 2010

Related U.S. Application Data

(60) Continuation of application No. 11/294,318, filed on Dec. 5, 2005, now Pat. No. 7,682,623, which is a continuation of application No. 10/392,071, filed on Mar. 19, 2003, now Pat. No. 6,994,863, which is a division of application No. 09/653,267, filed on Aug. 31, 2000, now Pat. No. 6,967,023.

(60) Provisional application No. 60/216,162, filed on Jul. 3, 2000.

(51) Int. Cl.
*A61K 7/00* (2006.01)
*A61K 7/48* (2006.01)
*A61K 31/74* (2006.01)
*A61K 7/06* (2006.01)

(52) U.S. Cl.
USPC ............... 424/401; 424/78.03; 424/78.06; 424/78.07; 424/70.1; 514/724; 514/859; 514/861; 514/863; 514/864; 514/880; 514/887

(58) Field of Classification Search
USPC ............... 424/401, 78.03, 78.06, 78.07, 70.1; 514/724, 859, 861, 863, 864, 880, 887
See application file for complete search history.

(56) References Cited

U.S. PATENT DOCUMENTS

| | | | |
|---|---|---|---|
| 1,159,250 A | 11/1915 | Moulton | |
| 1,666,684 A | 4/1928 | Carstens | |
| 1,924,972 A | 8/1933 | Beckert | |
| 2,085,733 A | 7/1937 | Bird | |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,767,712 A | 10/1956 | Waterman | |
| 2,968,628 A | 1/1961 | Reed | |
| 3,004,894 A | 10/1961 | Johnson et al. | |
| 3,062,715 A | 11/1962 | Reese et al. | |
| 3,067,784 A | 12/1962 | Gorman | |
| 3,092,255 A | 6/1963 | Hohman | |
| 3,092,555 A | 6/1963 | Horn | |
| 3,141,821 A | 7/1964 | Compeau | |
| 3,142,420 A | 7/1964 | Gawthrop | |
| 3,144,386 A | 8/1964 | Brightenback | |
| 3,149,543 A | 9/1964 | Naab | |
| 3,154,075 A | 10/1964 | Weckesser | |
| 3,178,352 A | 4/1965 | Erickson | |
| 3,236,457 A | 2/1966 | Kennedy et al. | |
| 3,244,589 A | 4/1966 | Sunnen | |
| 3,252,859 A | 5/1966 | Silver | |
| 3,261,695 A | 7/1966 | Sienkiewicz | |
| 3,263,867 A | 8/1966 | Lehmann | |
| 3,263,869 A | 8/1966 | Corsette | |
| 3,298,919 A | 1/1967 | Bishop et al. | |
| 3,301,444 A | 1/1967 | Wittke | |
| 3,303,970 A | 2/1967 | Breslau et al. | |
| 3,330,730 A | 7/1967 | Hernandez | |
| 3,333,333 A | 8/1967 | Noack | |
| 3,346,451 A | 10/1967 | Collins et al. | |
| 3,366,494 A | 1/1968 | Bower et al. | |
| 3,369,034 A | 2/1968 | Chalmers | |
| 3,377,004 A | 4/1968 | Wittke | |
| 3,384,541 A | 5/1968 | Clark et al. | |
| 3,395,214 A | 7/1968 | Mummert | |
| 3,395,215 A | 7/1968 | Schubert | |
| 3,401,849 A | 9/1968 | Weber, III | |
| 3,419,658 A | 12/1968 | Sanders | |
| 3,456,052 A | 7/1969 | Gordon | |
| 3,527,559 A | 9/1970 | Sliwinski | |
| 3,540,448 A | 11/1970 | Sunnen | |

(Continued)

FOREIGN PATENT DOCUMENTS

| | | |
|---|---|---|
| AU | 198780257 | 9/1986 |
| CA | 2422244 | 9/2003 |

(Continued)

OTHER PUBLICATIONS

U.S. Appl. No. 60/789,186, Tamarkin, Apr. 4, 2006.
U.S. Appl. No. 60/815,948, Tamarkin, Jun. 23, 2006.
U.S. Appl. No. 60/818,634, Friedman, Jul. 5, 2006.
U.S. Appl. No. 60/843,140, Tamarkin, Sep. 8, 2006.
U.S. Appl. No. 61/248,144, Tamarkin, Oct. 2, 2009.
U.S. Appl. No. 61/322,148, Tamarkin, Apr. 8, 2010.
U.S. Appl. No. 61/363,577, Eini, Jul. 12, 2010.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Oct. 21, 2011 at en.wikipedia.org/wiki/Minocycline, 7 pages.
"Reaction Rate" Accessed at en.wikipedia.org/wiki/Reaction_rate on Dec. 18, 2011, 6 pages.
'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.

(Continued)

*Primary Examiner* — Mina Haghighatian
(74) *Attorney, Agent, or Firm* — Fish & Richardson P.C.

(57) ABSTRACT

A pharmaceutical or cosmetic carrier or composition for topical application characterized by rheological properties which render the carrier or composition semi-solid at rest and a liquid upon application of shear forces thereto. The composition or carrier are prepared by mixing 1-25 percent of a solidifying agent and 75-99 percent of a hydrophobic solvent, by weight, wherein at least one of them has therapeutic or cosmetic benefits, in the presence or absence of a biologically active substance.

31 Claims, 1 Drawing Sheet

(56) References Cited

U.S. PATENT DOCUMENTS

| | | |
|---|---|---|
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |

| | | | | | |
|---|---|---|---|---|---|
| 5,100,917 A | 3/1992 | Flynn et al. | 5,603,940 A | 2/1997 | Candau et al. |
| 5,104,645 A | 4/1992 | Cardin et al. | 5,605,679 A | 2/1997 | Hansenne et al. |
| 5,112,359 A | 5/1992 | Murphy et al. | 5,608,119 A | 3/1997 | Amano et al. |
| 5,114,718 A | 5/1992 | Damani | 5,611,463 A | 3/1997 | Favre |
| 5,122,519 A | 6/1992 | Ritter | 5,612,056 A | 3/1997 | Jenner et al. |
| 5,130,121 A | 7/1992 | Kopolow et al. | 5,613,583 A | 3/1997 | Kono et al. |
| 5,133,972 A | 7/1992 | Ferrini et al. | 5,613,623 A | 3/1997 | Hildebrandt |
| 5,135,915 A | 8/1992 | Czarniecki et al. | 5,614,171 A | 3/1997 | Clavenna et al. |
| 5,137,714 A | 8/1992 | Scott | 5,614,178 A | 3/1997 | Bloom et al. |
| 5,143,717 A | 9/1992 | Davis | 5,635,469 A | 6/1997 | Fowler et al. |
| 5,156,765 A | 10/1992 | Smrt | 5,641,480 A | 6/1997 | Vermeer |
| 5,164,357 A | 11/1992 | Bartman et al. | 5,643,600 A | 7/1997 | Mathur |
| 5,164,367 A | 11/1992 | Pickart | 5,645,842 A | 7/1997 | Gruning et al. |
| 5,167,950 A | 12/1992 | Lins | 5,650,554 A | 7/1997 | Moloney |
| 5,171,577 A | 12/1992 | Griat et al. | 5,658,575 A | 8/1997 | Ribier et al. |
| 5,196,405 A | 3/1993 | Packman | 5,658,749 A | 8/1997 | Thornton |
| 5,204,093 A | 4/1993 | Victor | 5,658,956 A | 8/1997 | Martin et al. |
| 5,208,031 A | 5/1993 | Kelly | 5,663,208 A | 9/1997 | Martin |
| 5,217,707 A | 6/1993 | Szabo et al. | 5,672,634 A | 9/1997 | Tseng et al. |
| 5,219,877 A | 6/1993 | Shah et al. | 5,679,324 A | 10/1997 | Lisboa et al. |
| 5,221,696 A | 6/1993 | Ke et al. | 5,683,710 A | 11/1997 | Akemi et al. |
| 5,230,897 A | 7/1993 | Griffin et al. | 5,686,088 A | 11/1997 | Mitra et al. |
| 5,236,707 A | 8/1993 | Stewart, II | 5,693,258 A | 12/1997 | Tonomura et al. |
| 5,252,246 A | 10/1993 | Ding et al. | 5,695,551 A | 12/1997 | Buckingham et al. |
| 5,254,334 A | 10/1993 | Ramirez et al. | 5,700,396 A | 12/1997 | Suzuki et al. |
| 5,262,407 A | 11/1993 | Leveque et al. | 5,716,611 A | 2/1998 | Oshlack et al. |
| 5,266,592 A | 11/1993 | Grub et al. | 5,716,621 A | 2/1998 | Bello |
| 5,279,819 A | 1/1994 | Hayes | 5,719,122 A | 2/1998 | Chiodini et al. |
| 5,286,475 A | 2/1994 | Louvet et al. | 5,719,197 A | 2/1998 | Kanios et al. |
| 5,300,286 A | 4/1994 | Gee | 5,725,872 A | 3/1998 | Stamm et al. |
| 5,301,841 A | 4/1994 | Fuchs | 5,725,874 A | 3/1998 | Oda |
| 5,308,643 A | 5/1994 | Osipow et al. | 5,730,964 A | 3/1998 | Waldstreicher |
| 5,314,904 A | 5/1994 | Egidio et al. | 5,733,558 A | 3/1998 | Breton et al. |
| 5,322,683 A | 6/1994 | Mackles et al. | 5,733,572 A | 3/1998 | Unger et al. |
| 5,326,557 A | 7/1994 | Glover et al. | 5,747,049 A | 5/1998 | Tominaga |
| 5,344,051 A | 9/1994 | Brown | 5,753,241 A | 5/1998 | Ribier et al. |
| 5,346,135 A | 9/1994 | Vincent | 5,753,245 A | 5/1998 | Fowler et al. |
| 5,352,437 A | 10/1994 | Nakagawa et al. | 5,759,520 A | 6/1998 | Sachetto |
| 5,369,131 A | 11/1994 | Poli et al. | 5,759,579 A | 6/1998 | Singh et al. |
| 5,378,451 A | 1/1995 | Gorman et al. | 5,767,104 A | 6/1998 | Bar-Shalom et al. |
| 5,378,730 A | 1/1995 | Lee et al. | 5,773,410 A | 6/1998 | Yamamoto |
| 5,380,761 A | 1/1995 | Szabo Anna Z. et al. | 5,783,202 A | 7/1998 | Tomlinson et al. |
| 5,384,308 A | 1/1995 | Henkin | 5,788,664 A | 8/1998 | Scalise |
| 5,385,943 A | 1/1995 | Nazzaro-Porro | 5,792,448 A | 8/1998 | Dubief et al. |
| 5,389,676 A | 2/1995 | Michaels | 5,792,922 A | 8/1998 | Moloney et al. |
| 5,397,312 A | 3/1995 | Rademaker et al. | 5,797,955 A | 8/1998 | Walters |
| 5,398,846 A | 3/1995 | Corba et al. | 5,804,546 A | 9/1998 | Hall et al. |
| 5,399,205 A | 3/1995 | Shinohara et al. | 5,817,322 A * | 10/1998 | Xu .............................. 424/401 |
| 5,411,992 A | 5/1995 | Eini et al. | 5,824,650 A | 10/1998 | De Lacharriere et al. |
| 5,422,361 A | 6/1995 | Munayyer et al. | 5,833,960 A | 11/1998 | Gers-Barlag et al. |
| 5,429,815 A | 7/1995 | Faryniarz et al. | 5,833,961 A | 11/1998 | Siegfried et al. |
| 5,435,996 A | 7/1995 | Glover et al. | 5,837,270 A | 11/1998 | Burgess |
| 5,447,725 A | 9/1995 | Damani et al. | 5,840,744 A | 11/1998 | Borgman |
| 5,449,520 A | 9/1995 | Frigerio et al. | 5,840,771 A | 11/1998 | Oldham et al. |
| 5,451,404 A | 9/1995 | Furman | 5,843,411 A | 12/1998 | Hernandez et al. |
| 5,482,965 A * | 1/1996 | Rajadhyaksha ............... 514/452 | 5,846,983 A | 12/1998 | Sandborn et al. |
| 5,491,245 A | 2/1996 | Gruning et al. | 5,849,042 A | 12/1998 | Lim et al. |
| 5,500,211 A | 3/1996 | George et al. | 5,856,452 A | 1/1999 | Moloney et al. |
| 5,508,033 A | 4/1996 | Briand | 5,858,371 A | 1/1999 | Singh et al. |
| 5,512,555 A | 4/1996 | Waldstreicher | 5,865,347 A | 2/1999 | Welschoff |
| 5,514,367 A | 5/1996 | Lentini et al. | 5,866,040 A | 2/1999 | Nakama et al. |
| 5,514,369 A | 5/1996 | Salka et al. | 5,869,529 A | 2/1999 | Sintov et al. |
| 5,520,918 A | 5/1996 | Smith | 5,871,720 A | 2/1999 | Gutierrez et al. |
| 5,523,078 A | 6/1996 | Baylin | 5,877,216 A | 3/1999 | Place et al. |
| 5,527,534 A | 6/1996 | Myhling | 5,879,469 A | 3/1999 | Avram et al. |
| 5,527,822 A | 6/1996 | Scheiner | 5,881,493 A | 3/1999 | Restive |
| 5,529,770 A | 6/1996 | McKinzie et al. | 5,885,581 A | 3/1999 | Massand |
| 5,531,703 A | 7/1996 | Skwarek et al. | 5,889,028 A | 3/1999 | Sandborn et al. |
| 5,534,261 A | 7/1996 | Rodgers et al. | 5,889,054 A | 3/1999 | Yu et al. |
| 5,536,743 A | 7/1996 | Borgman | 5,891,458 A | 4/1999 | Britton et al. |
| 5,540,853 A | 7/1996 | Trinh et al. | 5,902,574 A | 5/1999 | Stoner et al. |
| 5,545,401 A | 8/1996 | Shanbrom | 5,902,789 A | 5/1999 | Stoltz |
| 5,567,420 A | 10/1996 | McEleney et al. | 5,905,092 A | 5/1999 | Osborne et al. |
| 5,576,016 A | 11/1996 | Amselem et al. | 5,910,382 A | 6/1999 | Goodenough et al. |
| 5,578,315 A | 11/1996 | Chien et al. | 5,911,981 A | 6/1999 | Dahms et al. |
| 5,585,104 A | 12/1996 | Ha et al. | 5,912,007 A | 6/1999 | Pan et al. |
| 5,589,157 A | 12/1996 | Hatfield | 5,914,122 A | 6/1999 | Otterbeck et al. |
| 5,589,515 A | 12/1996 | Suzuki et al. | 5,914,310 A | 6/1999 | Li et al. |
| 5,597,560 A | 1/1997 | Bergamini et al. | 5,922,331 A | 7/1999 | Mausner |

| | | | | | | |
|---|---|---|---|---|---|---|
| 5,925,669 | A | 7/1999 | Katz et al. | 6,344,218 | B1 | 2/2002 | Dodd et al. |
| 5,948,682 | A | 9/1999 | Moloney | 6,348,229 | B1 | 2/2002 | Eini et al. |
| 5,951,544 | A | 9/1999 | Konwitz | 6,358,541 | B1 | 3/2002 | Goodman |
| 5,951,989 | A | 9/1999 | Heymann | 6,364,854 | B1 | 4/2002 | Ferrer et al. |
| 5,951,993 | A | 9/1999 | Scholz et al. | 6,372,234 | B1 | 4/2002 | Deckers et al. |
| 5,952,373 | A | 9/1999 | Lanzendorfer et al. | 6,375,960 | B1 | 4/2002 | Simonnet et al. |
| 5,952,392 | A * | 9/1999 | Katz et al. ............... 514/724 | 6,382,982 | B1 | 5/2002 | Wilcox et al. |
| 5,955,414 | A | 9/1999 | Brown et al. | 6,383,471 | B1 | 5/2002 | Chen et al. |
| 5,959,161 | A | 9/1999 | Kenmochi et al. | 6,395,258 | B1 | 5/2002 | Steer |
| 5,961,957 | A | 10/1999 | McAnalley | 6,395,300 | B1 | 5/2002 | Straub et al. |
| 5,961,998 | A | 10/1999 | Arnaud et al. | 6,403,061 | B1 | 6/2002 | Candau et al. |
| 5,972,310 | A | 10/1999 | Sachetto | 6,403,069 | B1 | 6/2002 | Chopra et al. |
| 5,976,555 | A | 11/1999 | Liu et al. | 6,410,036 | B1 | 6/2002 | De Rosa et al. |
| 5,980,904 | A | 11/1999 | Leverett et al. | 6,423,323 | B2 | 7/2002 | Neubourg |
| 5,990,100 | A | 11/1999 | Rosenberg et al. | 6,428,772 | B1 | 8/2002 | Singh et al. |
| 5,993,846 | A | 11/1999 | Friedman et al. | 6,433,003 | B1 | 8/2002 | Bobrove et al. |
| 6,001,341 | A | 12/1999 | Genova et al. | 6,433,024 | B1 | 8/2002 | Popp et al. |
| 6,006,948 | A | 12/1999 | Auer | 6,433,033 | B1 | 8/2002 | Isobe et al. |
| 6,019,967 | A | 2/2000 | Breton et al. | 6,437,006 | B1 | 8/2002 | Yoon et al. |
| 6,024,942 | A | 2/2000 | Tanner et al. | 6,440,429 | B1 | 8/2002 | Torizuka et al. |
| 6,030,630 | A | 2/2000 | Fleury et al. | 6,447,801 | B1 | 9/2002 | Salafsky et al. |
| 6,033,647 | A | 3/2000 | Touzan et al. | 6,455,076 | B1 | 9/2002 | Hahn et al. |
| 6,039,936 | A | 3/2000 | Restle et al. | 6,468,989 | B1 | 10/2002 | Chang et al. |
| 6,042,848 | A | 3/2000 | Lawyer et al. | 6,479,058 | B1 | 11/2002 | McCadden |
| 6,045,779 | A | 4/2000 | Mueller et al. | 6,486,168 | B1 | 11/2002 | Skwierczynski et al. |
| 6,071,536 | A | 6/2000 | Suzuki et al. | 6,488,947 | B1 | 12/2002 | Bekele |
| 6,075,056 | A | 6/2000 | Quigley, Jr. et al. | 6,511,655 | B1 | 1/2003 | Muller et al. |
| 6,080,394 | A | 6/2000 | Lin et al. | 6,514,487 | B1 | 2/2003 | Barr |
| 6,087,317 | A | 7/2000 | Gee | 6,524,594 | B1 | 2/2003 | Santora et al. |
| 6,090,772 | A | 7/2000 | Kaiser et al. | 6,531,118 | B1 | 3/2003 | Gonzalez et al. |
| 6,093,408 | A | 7/2000 | Hasenoehrl et al. | 6,534,455 | B1 | 3/2003 | Maurin et al. |
| 6,096,756 | A | 8/2000 | Crain et al. | 6,536,629 | B2 | 3/2003 | van der Heijden |
| 6,110,477 | A | 8/2000 | Hernandez et al. | 6,544,530 | B1 | 4/2003 | Friedman |
| 6,110,966 | A | 8/2000 | Pollock | 6,544,562 | B2 | 4/2003 | Singh et al. |
| 6,113,888 | A | 9/2000 | Castro et al. | 6,547,063 | B1 | 4/2003 | Zaveri et al. |
| 6,116,466 | A | 9/2000 | Gueret | 6,548,074 | B1 | 4/2003 | Mohammadi |
| 6,121,210 | A | 9/2000 | Taylor | 6,562,355 | B1 | 5/2003 | Renault |
| 6,126,920 | A | 10/2000 | Jones et al. | 6,566,350 | B2 | 5/2003 | Ono et al. |
| 6,140,355 | A | 10/2000 | Egidio et al. | 6,582,679 | B2 | 6/2003 | Stein et al. |
| 6,146,645 | A | 11/2000 | Deckers et al. | 6,582,710 | B2 | 6/2003 | Deckers et al. |
| 6,146,664 | A | 11/2000 | Siddiqui | 6,589,509 | B2 | 7/2003 | Keller et al. |
| 6,162,834 | A | 12/2000 | Sebillotte-Arnaud et al. | 6,596,287 | B2 | 7/2003 | Deckers et al. |
| 6,165,455 | A | 12/2000 | Torgerson et al. | 6,599,513 | B2 | 7/2003 | Deckers et al. |
| 6,168,576 | B1 | 1/2001 | Reynolds | 6,620,773 | B2 | 9/2003 | Stork et al. |
| 6,171,347 | B1 | 1/2001 | Kunz et al. | 6,638,981 | B2 | 10/2003 | Williams et al. |
| 6,180,669 | B1 | 1/2001 | Tamarkin | 6,649,571 | B1 | 11/2003 | Morgan |
| 6,183,762 | B1 | 2/2001 | Deckers et al. | 6,649,574 | B2 | 11/2003 | Cardis et al. |
| 6,186,367 | B1 | 2/2001 | Harrold | 6,672,483 | B1 | 1/2004 | Roy |
| 6,187,290 | B1 | 2/2001 | Gilchrist et al. | 6,682,726 | B2 | 1/2004 | Marchesi et al. |
| 6,189,810 | B1 | 2/2001 | Nerushai et al. | 6,691,898 | B2 | 2/2004 | Hurray et al. |
| 6,190,365 | B1 | 2/2001 | Abbott et al. | 6,709,663 | B2 | 3/2004 | Espinoza |
| 6,204,285 | B1 | 3/2001 | Fabiano et al. | 6,723,309 | B1 | 4/2004 | Deane |
| 6,210,656 | B1 | 4/2001 | Touzan et al. | 6,730,288 | B1 | 5/2004 | Abram |
| 6,210,742 | B1 | 4/2001 | Deckers et al. | 6,753,000 | B2 | 6/2004 | Breton et al. |
| 6,214,318 | B1 | 4/2001 | Osipow et al. | 6,753,167 | B2 | 6/2004 | Moloney et al. |
| 6,214,788 | B1 | 4/2001 | Velazco et al. | 6,762,158 | B2 | 7/2004 | Lukenbach et al. |
| 6,221,381 | B1 | 4/2001 | Shelford et al. | 6,765,001 | B2 | 7/2004 | Gans et al. |
| 6,221,823 | B1 | 4/2001 | Crisanti et al. | 6,774,114 | B2 | 8/2004 | Castiel et al. |
| 6,224,888 | B1 * | 5/2001 | Vatter et al. ............... 424/401 | 6,777,591 | B1 | 8/2004 | Chaudhary et al. |
| 6,231,837 | B1 | 5/2001 | Stroud et al. | 6,790,435 | B1 | 9/2004 | Ma et al. |
| 6,232,315 | B1 | 5/2001 | Shafer et al. | 6,796,973 | B1 | 9/2004 | Contente et al. |
| 6,251,369 | B1 | 6/2001 | Stoltz | RE38,623 | E | 10/2004 | Hernandez et al. |
| 6,258,374 | B1 | 7/2001 | Friess et al. | 6,811,767 | B1 | 11/2004 | Bosch et al. |
| 6,271,295 | B1 | 8/2001 | Powell et al. | 6,834,778 | B2 | 12/2004 | Jinbo et al. |
| 6,274,150 | B1 | 8/2001 | Simonnet et al. | 6,843,390 | B1 | 1/2005 | Bristor |
| 6,287,546 | B1 | 9/2001 | Reich et al. | 6,875,438 | B2 | 4/2005 | Kraemer et al. |
| 6,294,550 | B1 | 9/2001 | Place et al. | 6,881,271 | B2 | 4/2005 | Ochiai et al. |
| 6,229,032 | B1 | 10/2001 | Hamilton | 6,890,567 | B2 | 5/2005 | Nakatsu et al. |
| 6,299,023 | B1 | 10/2001 | Arnone | 6,902,737 | B2 | 6/2005 | Quemin et al. |
| 6,299,900 | B1 | 10/2001 | Reed et al. | 6,911,211 | B2 * | 6/2005 | Eini et al. ............... 424/401 |
| 6,305,578 | B1 | 10/2001 | Hildebrandt et al. | 6,946,120 | B2 | 9/2005 | Wai-Chiu So et al. |
| 6,306,841 | B1 | 10/2001 | Place et al. | 6,946,139 | B2 | 9/2005 | Henning |
| 6,308,863 | B1 | 10/2001 | Harman | 6,951,654 | B2 | 10/2005 | Malcolm et al. |
| 6,319,913 | B1 | 11/2001 | Mak et al. | 6,955,816 | B2 | 10/2005 | Klysz |
| 6,328,950 | B1 | 12/2001 | Franzke et al. | 6,956,062 | B2 | 10/2005 | Beilfuss et al. |
| 6,328,982 | B1 | 12/2001 | Shiroyama et al. | 6,958,154 | B2 | 10/2005 | Andolino Brandt et al. |
| 6,333,362 | B1 | 12/2001 | Lorant | 6,967,012 | B2 | 11/2005 | Eini et al. |
| 6,335,022 | B1 | 1/2002 | Simonnet et al. | 6,967,023 | B1 * | 11/2005 | Eini et al. ............... 424/401 |
| 6,341,717 | B2 | 1/2002 | Auer | 6,968,982 | B1 | 11/2005 | Burns |

| | | | |
|---|---|---|---|
| 6,969,521 B1 | 11/2005 | Gonzalez et al. | |
| RE38,964 E | 1/2006 | Shillington | |
| 6,994,863 B2 * | 2/2006 | Eini et al. ............. 424/401 | |
| 7,002,486 B2 | 2/2006 | Lawrence | |
| 7,014,844 B2 | 3/2006 | Mahalingam et al. | |
| 7,021,499 B2 | 4/2006 | Hansen et al. | |
| 7,029,659 B2 | 4/2006 | Abram | |
| 7,060,253 B1 | 6/2006 | Mundschenk | |
| 7,078,058 B2 | 7/2006 | Jones et al. | |
| 7,083,799 B1 | 8/2006 | Giacomoni | |
| 7,137,536 B2 | 11/2006 | Walters et al. | |
| 7,195,135 B1 | 3/2007 | Garcia | |
| 7,222,802 B2 | 5/2007 | Sweeton | |
| 7,225,518 B2 | 6/2007 | Eidenschink et al. | |
| 7,226,230 B2 | 6/2007 | Liberatore | |
| 7,235,251 B2 | 6/2007 | Hamer et al. | |
| 7,270,828 B2 | 9/2007 | Masuda et al. | |
| 7,455,195 B2 | 11/2008 | Mekata | |
| 7,497,354 B2 | 3/2009 | Decottignies et al. | |
| 7,575,739 B2 | 8/2009 | Tamarkin et al. | |
| 7,645,803 B2 | 1/2010 | Tamarkin et al. | |
| 7,654,415 B2 | 2/2010 | van der Heijden | |
| 7,682,523 B2 | 3/2010 | Eini et al. | |
| 7,682,623 B2 * | 3/2010 | Eini et al. ............. 424/401 | |
| 7,700,076 B2 | 4/2010 | Tamarkin et al. | |
| 7,704,518 B2 | 4/2010 | Tamarkin et al. | |
| 7,793,807 B2 | 9/2010 | Goujon et al. | |
| 7,820,145 B2 | 10/2010 | Tamarkin et al. | |
| 7,960,416 B2 | 6/2011 | Sato et al. | |
| 2001/0006654 A1 | 7/2001 | Cannell et al. | |
| 2001/0027218 A1 | 10/2001 | Stern et al. | |
| 2001/0027981 A1 | 10/2001 | Vlodek | |
| 2001/0036450 A1 | 11/2001 | Verite et al. | |
| 2002/0002151 A1 | 1/2002 | Ono et al. | |
| 2002/0004063 A1 | 1/2002 | Zhang | |
| 2002/0013481 A1 | 1/2002 | Schonrock et al. | |
| 2002/0015721 A1 | 2/2002 | Simonnet et al. | |
| 2002/0032171 A1 | 3/2002 | Chen et al. | |
| 2002/0035046 A1 | 3/2002 | Lukenbach et al. | |
| 2002/0035070 A1 | 3/2002 | Gardlik et al. | |
| 2002/0035087 A1 | 3/2002 | Barclay | |
| 2002/0035182 A1 | 3/2002 | L'Alloret et al. | |
| 2002/0039591 A1 | 4/2002 | Dahle | |
| 2002/0044659 A1 | 4/2002 | Ohta | |
| 2002/0045659 A1 | 4/2002 | Michelet et al. | |
| 2002/0048798 A1 | 4/2002 | Avery et al. | |
| 2002/0058010 A1 | 5/2002 | Picard-Lesboueyries et al. | |
| 2002/0072544 A1 | 6/2002 | Miller et al. | |
| 2002/0090386 A1 | 7/2002 | Haslwanter et al. | |
| 2002/0098215 A1 | 7/2002 | Douin et al. | |
| 2002/0111281 A1 | 8/2002 | Vishnupad | |
| 2002/0117516 A1 | 8/2002 | Lasserre et al. | |
| 2002/0134376 A1 | 9/2002 | Castro et al. | |
| 2002/0136755 A1 | 9/2002 | Tyrrell et al. | |
| 2002/0143188 A1 | 10/2002 | Garvey et al. | |
| 2002/0153390 A1 | 10/2002 | Vlodek | |
| 2002/0165170 A1 | 11/2002 | Wilson et al. | |
| 2002/0182162 A1 | 12/2002 | Shahinpoor et al. | |
| 2002/0187181 A1 | 12/2002 | Godbey et al. | |
| 2002/0198136 A1 | 12/2002 | Mak et al. | |
| 2003/0006193 A1 | 1/2003 | Ikeda et al. | |
| 2003/0031693 A1 | 2/2003 | Breton et al. | |
| 2003/0053961 A1 | 3/2003 | Eccard | |
| 2003/0077297 A1 | 4/2003 | Chen et al. | |
| 2003/0078172 A1 | 4/2003 | Guiramand et al. | |
| 2003/0114520 A1 | 6/2003 | Pereira et al. | |
| 2003/0118515 A1 | 6/2003 | Jew et al. | |
| 2003/0130247 A1 | 7/2003 | Gans et al. | |
| 2003/0175232 A1 | 9/2003 | Elliott et al. | |
| 2003/0175315 A1 | 9/2003 | Yoo et al. | |
| 2003/0180347 A1 | 9/2003 | Young et al. | |
| 2003/0185839 A1 | 10/2003 | Podolsky | |
| 2003/0194379 A1 | 10/2003 | Brugger et al. | |
| 2003/0195128 A1 | 10/2003 | Deckman et al. | |
| 2003/0206955 A1 | 11/2003 | Sonneville-Aubrun et al. | |
| 2003/0215472 A1 | 11/2003 | Bonda et al. | |
| 2004/0018228 A1 | 1/2004 | Fischell et al. | |
| 2004/0028752 A1 | 2/2004 | Kamm et al. | |
| 2004/0038912 A1 | 2/2004 | Michelet et al. | |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |

| Publication No. | Date | Inventor |
|---|---|---|
| 2006/0108377 A1 | 5/2006 | Glynn et al. |
| 2006/0110418 A1 | 5/2006 | Johnson |
| 2006/0014990 A1 | 6/2006 | Bortz et al. |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0090558 A1 | 4/2009 | Tamarkin et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0221194 A1 | 9/2010 | Loupenok |
| 2011/0002857 A1 | 1/2011 | Tamarkin et al. |
| 2011/0002969 A1 | 1/2011 | Serraima et al. |
| 2011/0212033 A1 | 9/2011 | Tamarkin et al. |
| 2011/0268665 A1 | 11/2011 | Tamarkin et al. |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0 156 507 | 10/1985 |
| EP | 0 186 453 | 7/1986 |
| EP | 0 211 550 | 2/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 734 927 | 12/2006 |
| EP | 1 758 547 | 3/2007 |
| EP | 1 584 324 | 11/2007 |
| EP | 1 889 609 | 2/2008 |

| | | | | | |
|---|---|---|---|---|---|
| FR | 2 591 331 | 6/1987 | JP | 11501045 | 1/1999 |
| FR | 2 640 942 | 6/1990 | JP | 11250543 | 9/1999 |
| FR | 2 736 824 | 1/1997 | JP | 2000/017174 | 1/2000 |
| FR | 2 774 595 | 8/1999 | JP | 2000/080017 | 3/2000 |
| FR | 2 789 371 | 8/2000 | JP | 2000/128734 | 5/2000 |
| FR | 2 793 479 | 11/2000 | JP | 2000/191429 | 7/2000 |
| FR | 2 814 959 | 4/2002 | JP | 2000/239140 | 9/2000 |
| FR | 2 833 246 | 6/2003 | JP | 2000/351726 | 12/2000 |
| FR | 2 840 903 | 12/2003 | JP | 2000/354623 | 12/2000 |
| FR | 2 843 373 | 2/2004 | JP | 2001/002526 | 1/2001 |
| FR | 2 845 672 | 4/2004 | JP | 2001/019606 | 1/2001 |
| FR | 2 848 998 | 6/2004 | JP | 2001/072963 | 3/2001 |
| FR | 2 860 976 | 4/2005 | JP | 2002/012513 | 1/2002 |
| FR | 2 915 891 | 11/2008 | JP | 2002/047136 | 2/2002 |
| GB | 808 104 | 1/1959 | JP | 2002/524490 | 8/2002 |
| GB | 808 105 | 1/1959 | JP | 2002/302419 | 10/2002 |
| GB | 922 930 | 4/1963 | JP | 2003/012511 | 1/2003 |
| GB | 933 486 | 8/1963 | JP | 2003/055146 | 2/2003 |
| GB | 998 490 | 7/1965 | JP | 2004/047136 | 2/2004 |
| GB | 1 026 831 | 4/1966 | JP | 2004/250435 | 9/2004 |
| GB | 1 033 299 | 6/1966 | JP | 2004/348277 | 12/2004 |
| GB | 1 081 949 | 9/1967 | JP | 2005/314323 | 11/2005 |
| GB | 1 121 358 | 7/1968 | JP | 2005/350378 | 12/2005 |
| GB | 1 162 684 | 8/1969 | JP | 2006/008574 | 1/2006 |
| GB | 1 170 152 | 11/1969 | JP | 2006/036317 | 2/2006 |
| GB | 1 201 918 | 8/1970 | JP | 2006/103799 | 4/2006 |
| GB | 1 347 950 | 2/1974 | JP | 2006525145 | 11/2006 |
| GB | 1 351 761 | 5/1974 | JP | 2007/131539 | 5/2007 |
| GB | 1 351 762 | 5/1974 | JP | S48-92282 | 3/2012 |
| GB | 1 353 381 | 5/1974 | KR | 143232 | 7/1998 |
| GB | 1 376 649 | 12/1974 | KR | 2001/003063 | 1/2001 |
| GB | 1 397 285 | 6/1975 | RU | 2277501 | 6/2006 |
| GB | 1 408 036 | 10/1975 | UA | 66796 | 6/2004 |
| GB | 1 457 671 | 12/1976 | WO | 82/01821 | 6/1982 |
| GB | 1 489 672 | 10/1977 | WO | 86/05389 | 9/1986 |
| GB | 2 004 746 | 4/1979 | WO | 88/01502 | 3/1988 |
| GB | 1 561 423 | 2/1980 | WO | 88/01863 | 3/1988 |
| GB | 2 114 580 | 8/1983 | WO | 88/08316 | 11/1988 |
| GB | 2 153 686 | 8/1985 | WO | 89/06537 | 7/1989 |
| GB | 2 172 298 | 9/1986 | WO | 90/05774 | 5/1990 |
| GB | 2 206 099 | 12/1988 | WO | 91/11991 | 8/1991 |
| GB | 2 166 651 | 5/1996 | WO | 92/00077 | 1/1992 |
| GB | 2 337 461 | 11/1999 | WO | 92/05142 | 4/1992 |
| GB | 2 367 809 | 4/2002 | WO | 92/05763 | 4/1992 |
| GB | 2 406 330 | 3/2005 | WO | 92/11839 | 7/1992 |
| GB | 2 406 791 | 4/2005 | WO | 93/25189 | 12/1993 |
| IL | 49491 | 9/1979 | WO | 94/06440 | 3/1994 |
| IL | 152 486 | 5/2003 | WO | 96/03115 | 2/1996 |
| JP | 60001113 | 4/1978 | WO | 96/19921 | 7/1996 |
| JP | 55069682 | 5/1980 | WO | 96/24325 | 8/1996 |
| JP | 57044429 | 3/1982 | WO | 96/26711 | 9/1996 |
| JP | 56039815 | 4/1984 | WO | 96/27376 | 9/1996 |
| JP | 61275395 | 12/1986 | WO | 96/39119 | 12/1996 |
| JP | 62241701 | 10/1987 | WO | 97/03638 | 2/1997 |
| JP | 63119420 | 5/1988 | WO | 97/39745 | 10/1997 |
| JP | 1100111 | 4/1989 | WO | 98/17282 | 4/1998 |
| JP | 1156906 | 6/1989 | WO | 98/18472 | 5/1998 |
| JP | 2184614 | 7/1990 | WO | 98/19654 | 5/1998 |
| JP | 2255890 | 10/1990 | WO | 98/21955 | 5/1998 |
| JP | 4282311 | 10/1992 | WO | 98/23291 | 6/1998 |
| JP | 4312521 | 11/1992 | WO | 98/36733 | 8/1998 |
| JP | 5070340 | 3/1993 | WO | 98/52536 | 11/1998 |
| JP | 5213734 | 8/1993 | WO | 99/08649 | 2/1999 |
| JP | 6100414 | 4/1994 | WO | 99/20250 | 4/1999 |
| JP | H06-263630 | 6/1994 | WO | 99/37282 | 7/1999 |
| JP | 6329532 | 11/1994 | WO | 99/53923 | 10/1999 |
| JP | 2007/155667 | 6/1995 | WO | 00/09082 | 2/2000 |
| JP | 7215835 | 8/1995 | WO | 00/15193 | 3/2000 |
| JP | 2008/040899 | 2/1996 | WO | 00/23051 | 4/2000 |
| JP | 8501529 | 2/1996 | WO | 00/33825 | 6/2000 |
| JP | 8119831 | 5/1996 | WO | 00/38731 | 7/2000 |
| JP | 8165218 | 6/1996 | WO | 00/61076 | 10/2000 |
| JP | 8277209 | 10/1996 | WO | 00/76461 | 12/2000 |
| JP | 09 084855 | 3/1997 | WO | 01/05366 | 1/2001 |
| JP | 9099553 | 4/1997 | WO | 01/08681 | 2/2001 |
| JP | 9110636 | 4/1997 | WO | 01/10961 | 2/2001 |
| JP | 10114619 | 5/1998 | WO | 01/53198 | 7/2001 |
| JP | 3050289 | 9/1998 | WO | 01/54212 | 7/2001 |
| JP | 2010/332456 | 12/1998 | WO | 01/54679 | 8/2001 |

| | | |
|---|---|---|
| WO | 01/62209 | 8/2001 |
| WO | 01/70242 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | 02/15860 | 2/2002 |
| WO | 02/15873 | 2/2002 |
| WO | 02/28435 | 4/2002 |
| WO | 02/41847 | 5/2002 |
| WO | 02/43490 | 6/2002 |
| WO | 02/62324 | 8/2002 |
| WO | 02/78667 | 10/2002 |
| WO | 02/87519 | 11/2002 |
| WO | 03/000223 | 1/2003 |
| WO | 03/002082 | 1/2003 |
| WO | 03/013984 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | 2011/039637 | 4/2011 |
| WO | 2011/039638 | 4/2011 |

OTHER PUBLICATIONS

Adachi, Shuji. "Storage and Oxidative Stability of O/W/ Nano-emulsions." Foods Food Ingredients. J. Jpn. vol. 209, No. 11. 2004. 1 page.

Alcohol SDA 40B.http://www.pharmco-prod.com/pp./MSDS/SDA.sub.—40B.sub.—200.pdf Accessed Dec. 9, 2008, 2 pages.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400- Hydrogen Peroxide Pastes Used to Treat Infected Wounds,"Antimicrobial Agents and Chemotherapy, vol. 35, No. 9, pp. 1799-1803, 1991.

Anton, N. et al. "Water-in-Oil Nano-Emulsion Formation by the phase Method: A Novel and General Concept, a New Template for Nanoencapsulation," *Proceedings of the 33rd Annual Meeting and Exposition of the Controlled Release Society*, Jul. 2006, Vienna Austria, 2 pages.

Arct et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.corn/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry and Badal, "Stability of minocycline, doxycycline, and tetracycline stored in agar plates and microdilution trays," *Current Microbiology*, 1978, 1:33-36.

Barry, B.W. et al, Comparative bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychern/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel a.W., et al., "Bioavailability of Topically Administered Steroids: A 'Mass Balance' Technique," Journal of Investigative Dermatology, vol. 91, No. 1, Jul. 1988, pp. 29-33.

Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000) - Abstract, 1 page.

Carbowax 1000MSDS; http://www.sciencelab.com/xMSDS-Poly-ethylene.sub.—glycol.sub.—1000-9926-622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007) - Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (Nov.), p. S475 (1997), 2 pages.

Coetzee, "Acceptability and Feasibility of Micralax applicators and of methyl cellulose gel placebo for large-scale clinical trials of vaginal microbicides," NicolAIDS 2001, vol. 15, No. 14, pp. 1837-1842.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

D.W.A. Sharp Dictionary of Chemistry, Penguin Books, 1983, 3 pages.

Dalby, "Determination of Drug Solubility in Aerosol Propellants," Pharmaceutical Research, vol. 8, No. 9, 1991, pp. 1206-1209.

Dawber, et al., "Hypertrichosis in Females Applying Minoxidil Topical Solution and in Normal Controls", JEADV, 17:271-275 (2003).

Denatonium Benzoate http://www.newdruginfo.com/pharmaceopeia/usp28/v28230/usp28nf23s0.sub.--m- 22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

disorder. (2007). In the American Heritage Dictionary of the English Language. Retrieved from http://www.credoreference.com/entry/hmdictenglang/disorder. 1 page.

Draelos, Z. D. "Antiperspirants and the Hyperhidrosis Patients." Dermatologic Therapy. 2001. vol. 14. pages 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006; 111(2):145-51.

Edwards, "Imiquimod in Clinical Practice", J. Am Acad Dermatol., 43(1, Pt 2):512-517 (2000)—Abstract, 1 page.

Emulsifiers with HLB values. http://www.theherbarie.com/files/resources-center/formulating/Emulsifiers-.sub.—HLB.sub.--Values. pdf accessed Aug. 5, 2009 (3 pps).

Encyclopedia of Pharmaceutical Technology, Second Edition, vol. 3, Copyright 2002, 4 pages.

Esposito, E. et al. "Nanosystems for Skin Hydration: A Comparative Study." International Journal of Cosmetic Science. 29. 2007. pages. 39-47.

Ethanol, Accessed http://www.sigmaaldrich.com/catalog/ProductDetail.do?N4=E7023SIAL&N5=SEAR- CH.sub.—Concat.sub.—PNOBRAND.sub.--KEY&F=SPEC Dec. 9, 2008, 2 pages.

Ethylene Oxide Derivatives: An Essence of Every Industry. A definition of Emulsifier. Http://www.emulsifiers.In/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimiko-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irriadiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

Hall, Karla, "Diaper Area Hemangiomas: A Unique Set of Concerns," http://members.tripod.com/.about.Michelle.sub.—G/diaper.html, Dec. 1, 2008, 8 pages.

Hallstar. Retrieved online on Jun. 4, 2011. <URL:http://www.hallstar.com/pis.php?product=1H022>. 1 page.

Hargreaves, "Chemical Formulation, An Overview of Surfactant-Based Preparations Used in Everyday Life", *The Royal SocietyLV Chemistry*, pp. 114-115 (2003).

Harrison, et al., "Effects of cytokines and R-837, a cytokine inducer, on UV-irradiation augmented recurrent genital herpes in guinea pigs", Antiviral Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Hashim, et al. "Tinea versicolor and visceral leishmaniasis," Int J Dermatol., Apr. 1994; 33(4), pp. 258-259 (abstract only).

Heart Failure, the Merck Manual, 2008 <<http://www.merck.com/mmhe/sec03/ch025/ch025a.html>> 12 pages.

Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 pages).
Hormones. Http://www.greenwillowtree.com/Page.bok?file=libido.html. Jan 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
hydroxyethylcellulose. Http: //terpconnect.umd.edu/-choi/MSDS/Sigma-Aldrich/HYDROXYETHYL%20CELLULOSE, 5 pages, Jan. 14, 2004.
ICI Americas Inc. "The HLB System: A Time-Saving Guide to Emulsifier Selection." Mar. 1980. pages 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theall7c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kang, et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006).
Kim, "Stability of Minoxidil in Aqueous Solution", Yakhak Hoechi, 30(5):228-231 (1986)—Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." *J Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5):269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (Nov.), p. S475 (1997), 2 pages.
Licking Vaginal Dryness without a Prescription. Accessed http://www.estronaut.com/a/vag.sub.—dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Martindale. 33 ed. London, Bath Press, 2002. pp. 1073 and 1473.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Index, An Encyclopedia of Chemicals, Drugs, and Biologicals. 13$^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkylbenzoate.aspx. Printed Oct. 24, 2010. 1 page.
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
prevent. (2007). In The American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural 503-507 and synthetic triphylite," *J. of Power Sources*, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt a., "Malassezia furfur: a fungus belonging to the physiological skin flora and its relevance in skin disorders," Curtis., Jan. 1997; 59(1), pp. 21-4 (abstract).
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.

Sigma Aldrich, "HLB-Numbers in Lithography Nanopatterning," http://www.sigmaaldrich.com/materials-science/micro-and-nanoelectronics/l-ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen ÒTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 3pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pages. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatoll.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (Nov.), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pags. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate -1. Accute toxicity of hydrocortisone 17-butyrate 21-propionate and its analogues in mice, rats and dogs (author's trans), J Toxicol Sci., 1981 Jul. 6, 1981; Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb. 4, 2009, 4 pages, cited by other.
Tones-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.

Trofatter, "imiquimod in clinical Practice", European Journal of Dermatology, 8(7 Supp.):17-19 (1998)—Abstract, 1 page.

Tsai, et al., "Drug and Vehicle Deposition from Topical Applications: Use of in Vitro Mass Balance Technique with Minosidil Solutions", J. Pharm. Sci., 81(8):736-743 (1992)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Tzen, Jason T.C. et al. "Surface Structure and Properties of Plant Seed Oil Bodies." Department of Botany and Plant Sciences, University of California, Riverside, California 92521. Apr. 15, 1992. 9 pages.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

Yamada and Chung, "Crystal Chemistry of the Olivine-Type $Li(Mn_yFe_{1-y})PO_4$ and $(Mn_yFe_{1-y})PO4$ as Possible 4 V Cathopde Materials for Lithium Batteries," J. Electrochemical Soc., 2001, 148(8): A960-967.

"Coal tars and coal-tar pitches," Report on Carcinogens, Twelfth Edition, 2011, 3 pages.

Adisen et al. "Topical tetracycline in the 7:953-5 treatment of acne vulgaris," J Drugs Dermatol., 2008, 7:953-5.

Baskaran et al., "Poloxamer-188 improves capillary blood flow and tissue viability in a cutaneous burn wound," J. Surg. Res., 2001, 101(1):56-61.

Bell-Syer et al. "A systematic review of oral treatments for fungal infections of the skin of the feet," J. Dermatolog. Treat., 2001, 12:69-74.

Boehm et al. 1994, "Synthesis of high specific activity [.sup.3 H]-9-cis-retinoic acid and its application for identifying retinoids with unusual binding properties," J. Med. Chem., 37:408-414.

Carapeti et al., "Topical diltiazem and bethanechol decrease anal sphincter pressure and heal anal fissures without side effects," Dis Colon Rectum, 2000, 43(10):1359-62.

Cook and Mortensen, "Nifedipine for 43(3):430-1 treatment of anal fissures," Dis Colon Rectum, 2000, 43(3):430-1.

Dumortier et al., "A review of poloxamer 407 pharmaceutical and pharmacological characteristics," Pharmaceutical Res., 2006, 23(12):2709-2728.

Ebadi et al., "Healing effect of topical nifedipine on skin wounds of diabetic 11(1):19-22 rats," DARU, 2003, 11(1):19-22.

Effendy and Maibach. "Surfactants and Experimental Irritant Contact Dermatitis." Contact Dermatol., 1995, 33:217-225.

Elias and Ghadially, "The aged epidermal permeability barrier," Clinical Geriatric Medicine, Feb. 2002, pp. 103-120.

Fantin et al., "Critical influence of resistance to streptogramin B-type antibiotics on activity of RP 59500 (Quinupristin-dalfopristin) in experimental endocarditis due to Staphylococcus aureus," Antimicrob Agents and Chemothery,. 1999, 39:400-405.

Fluter et al., "Glycerol accelerates recovery of barrier function in vivo," Acta Derm. Venereol,. 1999, 79:418-21.

Garti et al. "Sucrose Esters microemulsions," J. Molec. Liquids, 1999, 80:253-296.

Hammer et al. "Anti-Microbial Activity of Essential Oils and other Plant Extracts," J. Applied Microbiology, 1999, 86:985-990.

Hwang et al. "Isolation and identification of mosquito repellents in Artemisia vulgaris" J. Chem. Ecol., 11: 1297-1306, 1985.

Knight et al., "Topical diltiazem ointment in the treatment of chronic anal fissure," Br. J. Surg., 2001, 88(4):553-6.

Kucharekova et al., "Effect of a lipid-rich emollient containing ceramide 3 in experimentally induced skin barrier dysfunction," Contact Dermatitis, Jun. 2002, pp. 331-338.

Leive et al, "Tetracyclines of various hydrophobicities as a probe for permeability of Escherichia coli outer membrane," Antimicrobial Agents and Chemotherapy, 1984, 25:539-544.

Luepke and Kemper, "The HET-CAM Test: An Alternative to the Draize Eye Test," FD Chem. Toxic., 1986, 24:495-196.

Osborne and Henke, "Skin Penetration Enhancers Cited in the Technical Literature," Pharm. Technology, Nov. 1997, pp. 58-86.

Padi. "Minocycline prevents the development of neuropathic pain, but not acute pain: possible anti-inflammatory and antioxidant mechanisms," Eur J. Pharmacol, 2008, 601:79-87.

Palamaras and Kyriakis, "Calcium antagonists in dermatology: a review of the evidence and research-based studies," Derm. Online Journal, 2005, 11(2):8.

Passi et al., Lipophilic antioxidants in human sebum and aging, Free Radical Research, 2002, pp. 471-477.

Perrotti et al., "Topical Nifedipine With Lidocaine Ointment vs. Active Control for Treatment of Chronic Anal Fissure," Dis Colon Rectum, 2002, 45(11):1468-1475.

Repa et al. "All-trans-retinol is a ligand for the retinoic acid receptors," Proc. Natl. Acad Sci, USA, 90:7293-7297, 1993.

Ruledge, "Some corrections to the record on insect repellents and attractants," J. Am. Mosquito Control Assoc, 1988, 4(4): 414-425.

Sakai et al., "Characterization of the physical properties of the stratum corneum by a new tactile sensor," Skin Research and Technology, Aug. 2000, pp. 128-134.

Schaefer, "Silicone Surfactants," Tenside, Surfactants, Deterg., 1990, 27(3): 154-158.

Simoni et al., "Retinoic acid and analogs as potent inducers of differentiation and aptosis. New promising chemopreventive and chemotherapeutic agents in oncology," Pure Appl Chem., 2001, 73(9):1437-1444.

Smith, "Hydroxy acids and skin again," Soap Cosmetics Chemical Specialties, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," European J. Pharm. Biopharm., 1998, 46(3):265-71.

Todd et al. "Volatile Silicone Fluids for Cosmetics," 91 Cosmetics and Toiletries, 1976, 27-32.

Torma et al., "Biologic activities of retinoic acid and 3, 4-dehydroretinoic acid in human keratinoacytes are similar and correlate with receptor affinities and transactivation properties," J. Invest. Dermatology, 1994, 102: 49-54.

USP23/NF 18 The United States Pharmacopeia: The National Formulary, US Pharmacopoeia, 1995, p. 10-14.

Van Slyke, "On the measurement of buffer values and on the relationship of buffer value to the dissociation constant of the buffer and the concentration and reaction of buffer value to the of the buffer solution," J. Biol. Chem., 1922, 52:525-570

Van Cutsem et al., "The antiinflammatory efects of ketoconazole," J. AM. ACAD. Dermatol., 1991, 25(2 pt 1):257-261.

Wang and Chen, "Preparation and surface active properties of biodegradable dextrin derivative surfactants," Colloids and Surfaces A: Physicochemical and Engineering Aspects, 2006, 281(1-3):190-193.

Weindl et al., "Hyaluronic acid in the treatment and prevention of skin diseases: molecular biological, pharmaceutical and clinical aspects," Skin Pharmacology and Physiology, 2004, 17: 207-213.

Xynos et al., "Effect of nifedipine on rectoanal motility," Dis Colon Rectum, 1996, 39(2):212-216.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5- hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

International Preliminary Examination Report from PCT/IL01/00025, dated Aug. 27, 2001, and International Search Report dated Jun. 22, 2001, 6 pages.

* cited by examiner

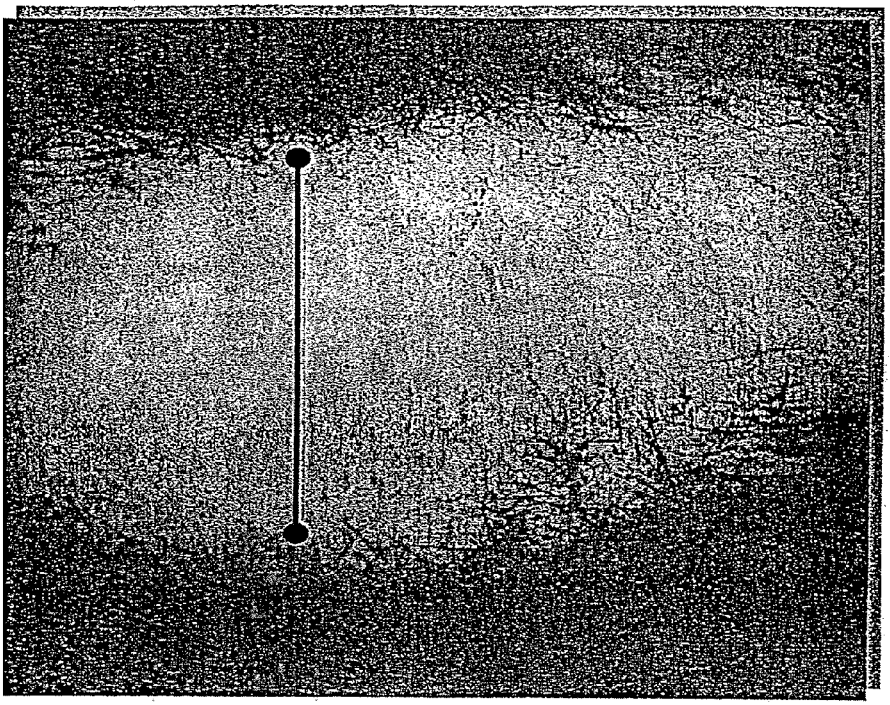
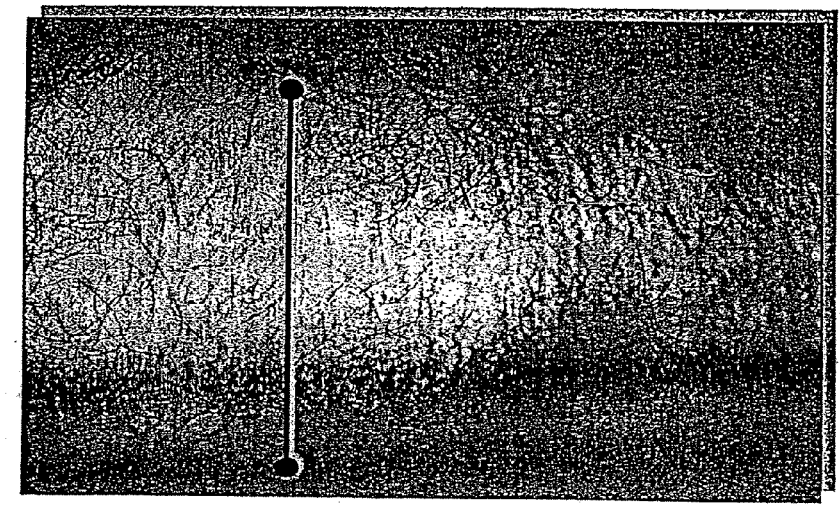
the effect of a Corticosteroid Composition in Corticosteroid Composition in a Psoriasis Patient
After 10 days TU-2100
Before Treatment

PHARMACEUTICAL COMPOSITION FOR TOPICAL APPLICATION

CROSS-REFERENCE TO RELATED APPLICATIONS

This application is a continuation under 35 U.S.C. §120 of U.S. patent application Ser. No. 11/294,318, filed Dec. 5, 2005, which is a continuation of U.S. patent application Ser. No. 10/392,071, filed on Mar. 19, 2003, now U.S. Pat. No. 6,994,863, which is a divisional of U.S. patent application Ser. No. 09/653,267, filed on Aug. 31, 2000, now U.S. Pat. No. 6,967,023, which is a non-provisional of U.S. Provisional Patent Application No. 60/216,162, filed Jul. 3, 2000, all of which applications are hereby incorporated by reference.

FIELD AND BACKGROUND OF THE INVENTION

The present invention relates to a pharmaceutical or cosmetic carrier or composition for topical application onto skin and/or mucosal membranes (e.g., the mucosa of the nose, mouth, eye, ear, vagina or rectum). More particularly, the present invention relates to (i) a cosmetic or pharmaceutical carrier or composition characterized by rheological properties which render the carrier or composition semi-solid at rest and liquid upon application of shear forces (e.g., spread forces) thereto; (ii) methods of preparing same; and (iii) methods of utilizing same for treating a variety of skin or mucosal membrane diseases or disorders.

Most of the skin or mucosal membrane diseases or disorders are the result of inflammation caused by inflammatory agents, such as, but not limited to, bacterial, fungal, viral, parasitic, autoimmune, allergic, hormonal and/or malignant inflammatory agents. The most common skin diseases or disorders include eczema, psoriasis and dermatitis, including contact dermatitis, atopic dermatitis and seborrheic dermatitis.

Eczema and dermatitis result from inflammatory processes that involve the upper dermis and epidermis of the skin. When eczema develops, the keratinocytes in the epidermis distend from one another and fluid is accumulated there amongst in a process known as spongiosis.

In chronic forms of eczema or dermatitis the main change include thickening of the epidermis, which leads to itching, roughening and scaling of the skin surface. The loss of water from the skin leads to inflammation of the horny layer, which later result in cracked and sore skin.

Dermatitis is further classified into contact dermatitis (allergic or non allergic), atopic dermatitis and seborrheic dermatitis.

Non allergic contact dermatitis occurs in response to skin irritants, such as acids, alkalis, oils, detergents and solvents.

Allergic contact dermatitis occurs as a result of sensitization to repeated exposure to an antigen. Allergic contact dermatitis appears in skin areas that were in direct contact with the antigen.

Atopic dermatitis, which affects mainly infants, is characterized by sensitization of the skin to a wide range of common antigens.

Seborrheic dermatitis affects the scalp and other hairy areas, the face, and flexural areas and results from yeast or bacteria induced inflammation. Most people suffer from dandruff which is a mild form of seborrheic dermatitis.

Psoriasis is a dominant autosomal inherited inflammatory disease characterized by enhanced proliferation of keratinocytes which proliferation leads to formation of scaly plaques on, for example, the knees, elbows, buttocks, and which are esthetically unpleasant and cause discomfort to the affected subject.

Skin diseases or disorders are usually treated by creams, gels or ointments containing antifungal agents, steroidal agents and/or antibacterial agents. In many instances such creams, gels and ointments are difficult to spread, result in a greasy and sticky appearance and are usually not appealing for use.

Genital infections are caused by fungal, viral and microbial agents. Genital infections are treated either systematically, or by the use of creams, ointments or pessaries, which usually leak or otherwise fail to spread well and lead to ineffective therapeutic concentration of the therapeutically active agent(s) therein.

Genital herpes infections are widespread from the 70's and apart from the discomfort they inflict, genital herpes infections may, in some cases, develop into severe disease. Presently, there is no effective medication for genital herpes.

Trichomoniasis is an infection of the urogenital tract caused due to infection by the protozoan *Trichomonas vaginalis*. Trichomoniasis is associated with uncomfort itching and vaginal excretion in women.

Candidiasis is caused by *Candida albicans* and results in itching in the genital area and white discharge therefrom.

Mucosal membrane inflammations can affect other organs such as for example, the eye. Conjunctivitis, caused by different types of bacteria, such as, but not limited to, *Staphylococcus aureus, Streptococcus pneumoniae* or *Haemophilus influenzae*, is generally treated with antibiotic ointments, e.g., bacitracin 500 U/g or gentamicin 0.3 percent ophthalmic ointment instilled into the affected eye. The compliance to these ointments is usually poor due to the sticky feeling they exert.

As is evident from the above descriptions, one of the important routes of administration of a drug for treating a skin or mucosal membrane is by topical application of a drug onto the skin or mucosal membrane. This method is useful for local treatment but it is also possible to apply pessaries via the rectum as an efficient delivery method of systemic agents that are not degraded in the intestine.

Many pharmaceutical carriers are presently known, most of them have disadvantages when topically applied onto the skin or mucosal membranes. For example, when ointments containing petroleum as a carrier are applied onto a skin wound, metabolic products and excreta from the wound cannot be easily removed therefrom because of the difficulty of passing through the hydrophobic petroleum barrier. In addition, the active drug ingredient, which is dissolved or dispersed in the petroleum carrier, is not efficiently absorbed into the wound tissue, thus, the efficacy of the drug is affected. Another example is ophthalmologic ointments, which are applied into the eye, and make the eye area sticky and uncomfortable. Moreover, in physiological aspect, petroleum restricts respiration of a wound tissue and is disturbing to the normal respiration of the skin.

Many groups of drugs including, for example, antibiotic, antifungal, antiinflammatory, anesthetic, analgesic, antiallergic, corticosteroid, retinoid and antiproliferative medications are preferably administered typically using a hydrophobic carrier such as petroleum. However, due to the undesirable consistency of petroleum and similar hydrophobic carriers, their topical use is limited. An additional disadvantage of petroleum-carrier including products relates to the greasy feeling following their topical application to the skin or mucosal membranes.

Besides petroleum, other hydrophobic pharmaceutical carriers are known, including liquid paraffin, lanolin, beeswax, vegetable oil, glycerin monostearate, higher alcohols, polyethylene glycol and some emulsifying agents. All of these agents either suffer the limitations described hereinabove with respect to petroleum or have undesirable (fast) flow properties.

Several hydrophobic liquids, e.g., mono- and poly-unsaturated oils from vegetable and marine sources, silicone oils, mineral oils, and liquid hydrophobic plant-derived oils are known for their therapeutic effects when applied topically. Oils may also contain essential nutritional constituents, such as oil-soluble vitamins (e.g., vitamin A and vitamin E), minerals and other therapeutically effective constituents. Administration of such therapeutic oils in a liquid form does not exert sufficient amounts of the therapeutic agents, because of the oil flow-spread properties. Other examples of therapeutic oils include mineral and silicone oils, which are useful for the treatment of skin dehydration and other medical diseases or disorders. These oils are also liquid at ambient temperature.

There is thus a widely recognized need for, and it would be highly advantageous to have a new pharmaceutical or cosmetic composition or carrier which is semi-solid at rest and which liquefies upon application of shear forces thereto, because such a pharmaceutical or cosmetic composition or carrier can be topically applied as a semi-solid onto an affected area and then turn into a liquid upon spreading, resulting in faster absorption and less greasiness and stickiness.

SUMMARY OF THE INVENTION

According to one aspect of the present invention there is provided a pharmaceutical or cosmetic carrier comprising, by weight, 1-25 percent of a solidifying agent and 75-99 percent of a hydrophobic solvent.

According to another aspect of the present invention there is provided a method of preparing a pharmaceutical or cosmetic carrier, the method comprising the steps of mixing a hydrophobic solvent and a solidifying agent at a temperature above a melting temperature of the solidifying agent so as to obtain a mixture containing 75-99 percent of the hydrophobic solvent by weight and 1-25 percent of the solidifying agent by weight; and cooling the mixture.

According to yet another aspect of the present invention there is provided a pharmaceutical or cosmetic composition comprising, by weight, 1-25 percent of a solidifying agent and 75-99 percent of a hydrophobic solvent, wherein at least one of the solidifying agent and the hydrophobic solvent has a therapeutic or cosmetic beneficial effect.

According to still another aspect of the present invention there is provided a pharmaceutical or cosmetic composition comprising (a) a pharmaceutical or cosmetic carrier containing, by weight, 1-25 percent of a solidifying agent and 75-99 percent of a hydrophobic solvent; and (b) a therapeutically or cosmetically effective amount of a biologically active substance.

According to an additional aspect of the present invention there is provided a method of preparing a pharmaceutical or cosmetic composition, the method comprising the steps of mixing a hydrophobic solvent and a solidifying agent at a temperature above a melting temperature of the solidifying agent so as to obtain a pharmaceutical or cosmetic mixture containing 75-99 percent of the hydrophobic solvent by weight and 1-25 percent of the solidifying agent by weight and further mixing into the mixture a therapeutically or cosmetically effective amount of a biologically active substance.

According to yet an additional aspect of the present invention there is provided a method of treating a disease or disorder of a skin or a mucosal membrane, the method comprising the step of topically administrating to the skin or the mucosal membrane a pharmaceutical or cosmetic composition containing, by weight, 1-25 percent of a solidifying agent and 75-99 percent of a hydrophobic solvent, wherein at least one of the solidifying agent and the hydrophobic solvent has a therapeutic or cosmetic beneficial effect.

According to a further aspect of the present invention there is provided a method of treating a disease or disorder of a skin or a mucosal membrane, the method comprising the step of topically administrating to the skin or the mucosal membrane a pharmaceutical or cosmetic composition containing (a) a pharmaceutical or cosmetic carrier containing, by weight, 1-25 percent of a solidifying agent and 75-99 percent of a hydrophobic solvent; and (b) a therapeutically or cosmetically effective amount of a biologically active substance.

According to further features in preferred embodiments of the invention described below, the solidifying agent is selected from the group consisting of at least one long chain fatty alcohol having at least 15 carbon atoms in its carbon backbone and at least one fatty acid, having at least 18 carbon atoms in its carbon backbone.

According to still further features in the described preferred embodiments the solidifying agent includes a substance selected such that under ambient conditions, the carrier is semi-solid at rest and liquefies upon application of shear forces thereto.

According to still further features in the described preferred embodiments the hydrophobic solvent is selected from the group consisting of at least one marine animal derived oil, at least one terrestrial animal derived oil, at least one mineral oil, at least one silicone oil and at least one plant-derived oil.

According to still further features in the described preferred embodiments the hydrophobic solvent includes an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojova oil.

According to still further features in the described preferred embodiments the hydrophobic solvent includes an oil selected from the group consisting of omega-3 oil and omega-6 oil.

According to still further features in the described preferred embodiments the solidifying agent has at least one alkyl group side chain in its carbon backbone.

According to still further features in the described preferred embodiments the carbon backbone of the fatty acid and/or the fatty alcohol has at least one hydroxyl group at position $\alpha$ or $\beta$.

According to still further features in the described preferred embodiments the carbon backbone of the fatty acid or the fatty alcohol has at least one hydroxyl group at positions 8-14.

According to still further features in the described preferred embodiments the solidifying agent includes a 12-hydroxy fatty acid.

According to still further features in the described preferred embodiments at least one of the solidifying agent and the hydrophobic solvent have a therapeutic or cosmetic beneficial effect.

According to still further features in the described preferred embodiments the skin or the mucosal membrane disease or disorder includes inflammation caused by an inflammatory agent selected from the group consisting of a bacterial inflammatory agent, a fungal inflammatory agent, a viral inflammatory agent, a parasitic inflammatory agent, an autoimmune inflammatory agent, an allergic inflammatory agent, a hormonal inflammatory agent and a malignant inflammatory agent.

According to still further features in the described preferred embodiments the skin disease or disorder is selected from the group consisting of psoriasis, acne, seborrhea, seborrheic dermatitis, alopecia and excessive hair growth, itching, wounds, burns, cuts, ulcers, seborrheic dermatitis of the face and trunk, seborrheic blepharitis, contact dermatitis, stasis dermatitis and exfoliative dermatitis.

According to still further features in the described preferred embodiments the statis dermatitis is selected from the group consisting of gravitational eczema, varicose eczema and the exfoliative dermatitis is erythroderma.

According to still further features in the described preferred embodiments the biologically active substance is selected from the group consisting of an antibiotic agent, a free radical generating agent, an antifungal agent, an antiviral agent, a non-nucleoside reverse transcriptase inhibitor, a nucleoside-analog reverse transcriptase inhibitor, a protease inhibitor, a protease inhibitor, a non-steroidal antiinflammatory drug, an immunosuppressant, an antihistamine agent, an antiinflammatory agent, a retinoid agent, a tar agent, an antipruritics agent and a scabicide agent.

According to still further features in the described preferred embodiments (a) the antibiotic agent is selected from the group consisting of chloramphenicol, tetracyclines, synthetic and semi-synthetic penicillins, beta-lactames, quinolones, fluoroquinolones, macrolide antibiotics, peptide antibiotics, cyclosporines, erythromycin and clindamycin; (b) the free radical generating agent is benzoyl peroxide; (c) the antifungal agent is selected from the group consisting of azoles, diazole, triazole, miconazole, fluconazole, ketoconazole, clotrimazole, itraconazole griseofulvin, ciclopirox, amorolfine, terbinafine, Amphotericin B and potassium iodide; (d) the antiviral agent is selected from the group of flucytosine (5FC), Vidarabine, acyclovir and Gancyclovir; (e) the nucleoside-analog reverse transcriptase inhibitor is selected from the group consisting of Zidovudine, Stavudine and Lamivudine; (f) the non-nucleoside reverse transcriptase inhibitor is selected from the group consisting of Nevirapine and Delavirdine; (g) the protease inhibitor is selected from the group consisting of Saquinavir, Ritonavir, Indinavir, Nelfinavir, Ribavirin Amantadine, Rimantadine and Interferon; (h) the immunosuppressant is selected from the group consisting of Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene; (i) the antiinflammatory agent is a vitamin B3 derivative; (j) the retinoid agent is selected from the group consisting of isotretinoin, adapalene and tretinoin; (k) the tar agent is selected from the group consisting of coal tar and cade oil; (l) the antihistamine agent is doxepine hydrochloride; (m) the antipruritic agent is crotampiton; and (n) the scabicide agent is selected from the group consisting of benzyl benzoate, malathion and crotamiton.

According to still further features in the described preferred embodiments the biologically active substance is effective in the treatment of psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis or exfoliative dermatitis.

According to still further features in the described preferred embodiments the statis dermatitis is selected from the group consisting of gravitational eczema; varicose eczema, whereas the exfoliative dermatitis is erythroderma.

The present invention successfully addresses the shortcomings of the presently known configurations by providing a biologically active carrier or composition, which is semi solid at rest and liquefies upon application of shear forces thereto, which is therefore easy to spread, highly absorbable, non greasy and non-sticky and which can be used for the treatment of a great number of diseases and syndromes affecting the skin and mucosal membranes.

BRIEF DESCRIPTION OF THE DRAWINGS

The invention is herein described, by way of example only, with reference to the accompanying drawing.

FIG. 1 is a photograph demonstrating the therapeutic effects of a corticosteroid composition prepared in accordance with the teachings of the present invention administered twice a day for 10 days, to a psoriasis patient. The composition was prepared as described in Example 1. The photograph clearly demonstrates a reduction in the psoriatic plaques size following the course of treatment.

DESCRIPTION OF THE PREFERRED EMBODIMENTS

The present invention is of (i) a pharmaceutical or cosmetic carrier or composition for topical application, preferably characterized by rheological properties which render the carrier or composition a semi-solid at rest and a liquid upon application of shear forces thereto; (ii) methods of preparing same; and (iii) methods of utilizing same for treating skin or mucosal membrane diseases or disorders.

The principles and operation of the present invention may be better understood with reference to the accompanying descriptions and examples.

Before explaining at least one embodiment of the invention in detail, it is to be understood that the invention is not limited in its application to the details of composition set forth in the following description or examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a pharmaceutical or cosmetic carrier comprising, by weight, 1-25 percent of a solidifying agent and 75-99 percent of a hydrophobic solvent, which solvent per se is typically liquid at ambient temperature.

As used herein in the specification and in the claims section that follows, the term "carrier" means a base which is, as is defined in the Collins dictionary, the main ingredient of a mixture. Thus, as used herein a "pharmaceutical carrier" is a pharmaceutical base which is used in the preparation of pharmaceutical compositions, whereas a "cosmetic carrier" is a cosmetic base which is used in the preparation of cosmetic compositions.

According to another aspect of the present invention there is provided a method of preparing a pharmaceutical or cosmetic carrier. The method according to this aspect of the invention is effected by mixing a hydrophobic solvent and a solidifying agent at a temperature above a melting temperature of the solidifying agent so as to obtain a mixture containing 75-99 percent of the hydrophobic solvent by weight and 1-25 percent of the solidifying agent by weight; and cooling the mixture, e.g., to room temperature. Preferably, prior to the step of mixing, both the hydrophobic solvent and the solidifying agent are brought to the temperature above the melting temperature of the solidifying agent.

According to still another aspect of the present invention there is provided a pharmaceutical or cosmetic composition comprising, by weight, 1-25 percent of a solidifying agent and 75-99 percent of a hydrophobic solvent, wherein at least one of the solidifying agent and/or the hydrophobic solvent has a therapeutic or cosmetic beneficial effect.

According to yet another aspect of the present invention there is provided a method of preparing a pharmaceutical or cosmetic composition. The method according to this aspect of the invention is effected by mixing a hydrophobic solvent and a solidifying agent at a temperature above a melting temperature of the solidifying agent so as to obtain a mixture containing 75-99 percent of the hydrophobic solvent by weight and 1-25 percent of the solidifying agent by weight; and cooling the mixture, e.g., to room temperature. Preferably, prior to the step of mixing, both the hydrophobic solvent and the solidifying agent are brought to the temperature above the melting temperature of the solidifying agent, e.g., 60-80° C.

Thus, the present invention offers a method of treating a disease or disorder of a skin or a mucosal membrane, such as, but not limited to, a mucosa of a nose, a mucosa of a mouth, a mucosa of an eye, a mucosa of an ear, a mucosa of a vagina and a mucosa of a rectum. The method according to this aspect of the present invention is effected by topically administrating to the skin or the mucosal membrane a pharmaceutical or cosmetic composition containing, by weight, 1-25 percent of a solidifying agent and 75-99 percent of a hydrophobic solvent, wherein at least one of the solidifying agent and the hydrophobic solvent has a therapeutic or cosmetic beneficial effect.

Most preferably, the amount of the solidifying agent in a pharmaceutical or cosmetic carrier according to the present invention is about 4 percent to about 12 percent, whereas the amount of the hydrophobic solvent is about 88 percent to about 96 percent of the total weight of the carrier. As used herein the term about refers to ±20%.

According to a preferred embodiment of the present invention, the solidifying agent includes at least one long chain fatty alcohol having at least 15 carbon atoms in its carbon backbone and/or at least one fatty acid, having at least 18 carbon atoms in its carbon backbone. Preferably, the solidifying agent has at least one alkyl group side chain in its carbon backbone. Additionally or alternatively, the carbon backbone of the fatty acid or the fatty alcohol has at least one hydroxyl group at position α and β. Still additionally or alternatively, the carbon backbone of the fatty acid or the fatty alcohol has at least one hydroxyl group at positions 8-14. According to presently preferred embodiments of the invention, the solidifying agent preferably includes a 12-hydroxy fatty acid.

According to another preferred embodiment of the present invention, the solidifying agent includes a substance selected such that ambient conditions, the carrier is semi-solid at rest and liquefies upon application of shear forces thereto, i.e., has thixotropic properties.

As mentioned above, preferred solidifying agents, according to the present invention, include fatty alcohols having 15 or more carbons in their carbon chain, such as acetyl alcohol and stearyl alcohol (or mixtures thereof). Other examples of fatty alcohols include arachidyl alcohol (C20), behenyl alcohol (C22), 1-triacontanol (C30), as well as alcohols with longer carbon chains (e.g., up to C50). The concentration of the fatty alcohol, required to obtain the thixotropic properties is inversely related to the length of its carbon chains.

Fatty alcohols, derived from beeswax, comprising a mixture of alcohols, where the majority have at least 20 carbon atoms in their carbon chain, are especially suited as solidifying agents according to the present invention.

Another preferred class of solidifying agents includes fatty acids having 18 or more carbons in their carbon chain, such as and stearic acid, arachidic acid (C20), behenic acid (C22), octacosanoic acid (C28), as well as fatty acids with longer carbon chains (e.g., up to C50), or mixtures thereof.

The concentration of the fatty acid required to obtain a thickened carrier is inversely related to the length of its carbon chains. Stearic acid, for example, exerts a considerable thickening effect at about 10 percent concentration, whereas behenic acid would obtain the same thickening effect at a 5 percent concentration.

Optionally, the carbon atom chain of the fatty alcohol or the fatty acid may have at least one double bond.

A further class of solidifying agent according to the present invention comprises long chain fatty alcohols or fatty acids, wherein the carbon atom chain is branched. In an additional preferred class of solidifying agents, the carbon chain of the fatty acid is substituted with a hydroxyl group, e.g., 12 hydroxy stearic acid.

An important property of the fatty alcohols and fatty acids used in context of the carrier and composition of the present invention is related to their therapeutic properties per se. Long chain saturated and mono unsaturated fatty alcohols, e.g., stearyl alcohol, erycyl alcohol, arachidyl alcohol and docosanol have been reported to possess antiviral, antiinfective, antiproliferative and antiinflammatory properties (see, U.S. Pat. No. 4,874,794, which is incorporated herein by reference). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess antiinfective characteristics. Thus, the pharmaceutical or cosmetic carrier of the present invention provides an extra therapeutic or cosmetic benefit in comparison with currently used vehicles, such as petroleum, which are inert and non-active.

According to still another preferred embodiment of the present invention, the hydrophobic solvent includes at least one marine animal derived oil, at least one terrestrial animal derived oil, at least one mineral oil, at least one silicone oil and/or at least one plant-derived oil. Examples include, but are not limited to, olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and/or jojova oil.

As used herein "tea tree oil" or "melaleuca oil" both refer to distillates of the leaves of the Australian tree, *Melaleuca alternifolia*. Tea tree oil is assigned the Chemical Abstract number 68647-73-4 and is commercially available from a variety of sources. Tea tree oil is recognized as having properties as a solvent, antiseptic, antibacterial, antifungal, and pain reliever, as well as other uses. *Melaleuca* oil has been used in soaps, shampoos, hand creams, tooth pastes, and household cleaners, as well as for treatment of warts and oral candidiasis.

A particularly preferred class of oils to be used in context of the present invention include poly-unsaturated oils which contains omega-3 and omega-6 fatty acids. Thus, in a presently most preferred embodiment of the present invention the carrier contains at least 6 percent omega-3 oil and/or omega-6 oil.

The above described pharmaceutical or cosmetic carrier may be used in the preparation of a pharmaceutical or cosmetic composition comprising (a) a pharmaceutical or cosmetic carrier containing, by weight, 1-25 percent of a solidifying agent and 75-99 percent of a hydrophobic solvent, which is typically liquid at ambient temperature; and (b) a therapeutically or cosmetically effective amount of a biologically active substance. Preferably, at least one of the solidifying agent and the hydrophobic solvent has a therapeutic or cosmetic beneficial effect.

As used herein in the specification and in the claims section that follows the phrase "biologically active substance" refers to an active ingredient which has a therapeutic or cosmetic effect following its administration to an organism (human or animal). The therapeutic or cosmetic effect can be curing, minimizing, preventing or ameliorating a disease or disorder, or improving the physical appearance and aesthetics (e.g., skin hydration) or may have any other therapeutic or cosmetic beneficial effect. The biologically active substance may be, for example, a drug, a vitamin or a vaccine. Thus, the biologically active substances employed in context of the present invention are generally selected from the broad categories of medicaments, agricultural products and cosmetic products. The biologically active substance may be a single drug or a combination of drugs that are dissolved or spread in the carrier of the present invention. Therefore, they are usually, yet not obligatorily, hydrophobic. The concentration of the substance is selected so as to exert its therapeutic or cosmetic effect.

According to another aspect of the invention there is provided a method of preparing a pharmaceutical or cosmetic composition. The method according to this aspect of the present invention is effected by (a) mixing a hydrophobic solvent and a solidifying agent at a temperature above a melting temperature of the solidifying agent so as to obtain a pharmaceutical or cosmetic mixture containing 75-99 percent of the hydrophobic solvent by weight, and 1-25 percent of the solidifying agent by weight; and (b) further mixing into the carrier mixture a therapeutically or cosmetically effective amount of a biologically active substance. Preferably, prior to the step of mixing, both the hydrophobic solvent and the solidifying agent are brought to the temperature above the melting temperature of the solidifying agent, e.g., 60-80° C.

According to a preferred embodiment of this aspect of the present invention the biologically active substance is an antibiotic agent, e.g., chloramphenicol, tetracyclines, synthetic and semi-synthetic penicillins, beta-lactames, quinolones, fluoroquinolones, macrolide antibiotics, peptide antibiotics, cyclosporines, erythromycin and clindamycin; a free radical, e.g., benzoyl peroxide; a generating agent; an antifungal agent, e.g., azoles, diazoles, triazoles, miconazole, fluconazole, ketoconazole, clotrimazole, itraconazole griseofulvin, ciclopirox, amorolfine, terbinafine, Amphotericin B and potassium iodide; an antiviral agent, e.g., flucytosine (5FC), Vidarabine, acyclovir and Gancyclovir; a non-nucleoside reverse transcriptase inhibitor, Nevirapine and Delavirdine; a nucleoside-analog reverse transcriptase inhibitor, a protease inhibitor, e.g., e.g., Zidovudine, Stavudine and Lamivudine, a protease inhibitor, e.g., Saquinavir, Ritonavir, Indinavir, Nelfinavir, Ribavirin Amantadine, Rimantadine and Interferon; a non-steroidal antiinflammatory drug, e.g., Voltarene; an immuno, e.g., Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene; an antihistamine, e.g., doxepine hydrochloride; an antiinflammatory agent, e.g., vitamin B3 or a derivative thereof; a retinoid agent, e.g., isotretinoin, adapalene and tretinoin; a tar agent, e.g., coal tar and cade oil; an antipruritics agent, e.g., crotampiton; or a scabicide agent, e.g., benzyl benzoate, malathion and crotamiton.

The biologically active substance is preferably selected effective in the treatment of a disease or disorder, such as, but not limited to, psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis (e.g., gravitational eczema, varicose eczema) or exfoliative dermatitis (e.g., erythroderma).

Thus, the present invention offers another method of treating a disease or disorder of a skin or a mucosal membrane, such as, but not limited to, a mucosa of a nose, a mucosa of a mouth, a mucosa of an eye, a mucosa of an ear, a mucosa of a vagina and mucosa of a rectum. The method is effected by topically administrating thereto a pharmaceutical or cosmetic composition containing (a) a pharmaceutical or cosmetic carrier containing, by weight, 1-25 percent of a solidifying agent and 75-99 percent of a hydrophobic solvent, which is typically liquid at ambient temperature; and (b) a therapeutically or cosmetically effective amount of a biologically active substance.

The pH of the composition or carrier of the present invention is preferably maintained in the range of about pH 5.5-7.0. Acids, bases, and buffers can be used according to methods well known in the art for adjusting the pH of the carrier or composition.

Pharmaceutical compositions manufactured using the carrier according to the present invention are very easy to use. When applied on the afflicted body surface of humans or animals, they are in a semi-solid state, allowing free application without spillage. Upon further application of a mechanical force, e.g., by rubbing the composition onto the body surface, it freely spreads on the surface and is rapidly absorbed. The ease of the application is demonstrated herein in Example 3, where it was compared, in a double blind test to a commercial hydrocortisone preparation. The subjects' score regarding their feeling about the preparation (e.g., the greasiness, stickiness, absorption, penetration, ease of spreading and lack of shiny look) was significantly higher than the score for the commercial preparation.

Additional particulars concerning the use of a variety of biologically active substances in context of the present invention, advantages of the present invention over prior art designs and a variety of applications of the present invention are provided hereinafter.

Treatment of Wounds:

The present invention may find special advantages in the treatment of wounds. Skin wounds which can be treated using the compositions of the present invention include burn wounds, sunburn, cuts, abrasions, acute and chronic wounds and the like. Treatment of burn, ulcers, acute and chronic wounds typically is directed to keeping the wound as clean as possible and making the patient as comfortable as possible. It has been recognized in this respect that keeping the wound moist is advantageous to patient comfort. While maintaining a moist environment will effect some cooling of the tissue, it would be advantageous to be able to decrease the intradermal temperature of a burn wound, which would help to alter the progression of the tissue damage due to heat within the tissues.

Accordingly, it would be advantageous to provide a method for improved treatment of a burn wound that permits significant lowering of the intradermal temperature of the burn wound such that the extent of the burn wound may be limited. Compositions which have antimicrobial agents combined with agents that lead to cooling effect, and which are devoid of adherence to the wound offer relief to people who are suffering from burns or ulcers. The present invention provides a protective moisture barrier to contribute to the sterility of the dressing and to maintain the moistness of the dressing. Sterility is enhanced by the bacteriostatic properties of the wound treatment composition, as well as the shielding action of the barrier's physical presence. An additional barrier to bacteria and contamination is the packaging utilized with the present invention and which is addressed in more detail below.

The wound treatment composition of the present invention comprises as the hydrophobic solvent, for example without limitation, tea tree oil, melaleuca oil and other ingredients in a thixotropic gel formulation. As stated hereinabove, Tea tree oil, or *Melaleuca alternifolia*, is a natural plant extract. The unique wound treatment composition, in addition to creating a moist, soothing environment, is also inherently bacteriostatic. It helps leave the surface of wounds clean and odor free. The odor of chronic wounds is a major concern of health care workers and caregivers. The effectiveness of *Melaleuca* is increased in the presence of blood and organic material, rather than decreased as is the case with other bacteriostatic products. *Melaleuca* oil is a natural oil which is considered to be safe and effective on all kinds of cuts and abrasions, surgical wounds, diabetic and mouth ulcers and foot fungi.

The application of the composition of the present invention onto cuts, wounds, burns and ulcers is beneficial both in the cure of an infection or in the protection of the skin from infection. In all such cases, the composition of the present invention is easy to use, being semi-solid when applied and becoming liquid instantly upon rubbing onto the skin.

Suppositories:

For treatment of vaginal infections, suppositories provide an effective mode for administration of a therapeutic agent. Although suppositories have attained some success, they have some disadvantages. Most of the current commercial vaginal suppositories, either melt or dissolve in the vaginal tract into an oily or aqueous liquid. This resulting liquid in turn tends to leak out or is expelled out of the vaginal cavity resulting either in soiled clothing and/or inferior efficacy.

Accordingly, it is an object of the present invention to provide an effective antifungal suppository formulation, which overcomes the noted disadvantages associated with the prior art suppositories.

The suppository formulation of the invention is useful in treating vaginal fungus infections in mammalian species, such as humans, cats, dogs and the like. The suppository formulation will be easily inserted into the vaginal cavity and will melt at body temperature soon after insertion. Upon melting, the suppository turns into a gel/cream like consistency, which will adheres to the vaginal membrane thereby providing prolonged duration of effectiveness.

As mentioned above, a pharmaceutical or cosmetic composition in accordance with the teachings of the present invention may include a biologically active substance. The following provides some examples.

Antiviral Agents:

The carrier or composition of the present invention is beneficial in the treatment of viral infections. For example, cold sores are caused by the herpes simplex Type 1 virus and are sometimes referred to as facial herpes. Mollusca are small viral growths that appear singly or in groups on the face, trunk, lower abdomen, pelvis, inner thighs or penis. Shingles (herpes zoster), which usually only occurs once in a lifetime, appears as a rash (clusters of blisters with a red base). It is caused by the same virus responsible for chickenpox. Warts are a common, benign skin tumor caused by viral infection. Eye viral infections, such as viral conjunctivitis is highly contagious and spreads by droplet, fomites, and hand-to-eye inoculation.

Viral infections are currently treated with various antiviral agents, as is summarized in Table 1 below:

TABLE 1

Antiviral drugs

| Drug | Viruses | Chemical Type |
|---|---|---|
| Vidarabine | Herpesviruses | Nucleoside analog |
| Acyclovir | Herpes simplex (HSV) | Nucleoside analog |
| Gancyclovir | Cytomegalovirus (CMV) | Nucleoside analog |
| Nucleoside-analog reverse transcriptase inhibitors (NRTI): AZT (Zidovudine), ddI (Didanosine), ddC (Zalcitabine), d4T (Stavudine), 3TC (Lamivudine) | Retroviruses (HIV) | Nucleoside analog |
| Non-nucleoside reverse transcriptase inhibitors (NNRTI): Nevirapine, Delavirdine | Retroviruses (HIV) | Nucleoside analog |
| Protease Inhibitors: Saquinavir, Ritonavir, Indinavir, Nelfinavir | HIV | Peptide analog |
| Ribavirin | Broad spectrum: HCV, HSV, measles, mumps, Lassa fever | Triazole carboxamide |
| Amantadine/Rimantadine | Influenza A strains | Tricyclic amine |
| Interferons | Hepatitis B and C | Protein |

It will be appreciated that the intrinsic antiviral effects of the solidifying agents, e.g., fatty alcohols and acids, provides a synergistic effect that will result in a higher therapeutic response.

Antiparasite Agents:

The biologically active substance contained in a composition of the present invention in a therapeutically effective amount may be an antiparasite agent, such as, but not limited to, hexachlorobenzene, carbamate, naturally occurring pyrethroids, permethrin, allethrin, malathion, piperonyl butoxide or mixtures of these drugs.

Antimicrobial Agents:

Antimicrobial agents, also referred to as germicidal agents, which may be used in compositions of the present invention include phenols, including cresols and resorcinols. Antibacterial compositions according to the present invention may be used to treat infections of the skin. An example of a very common skin infection is acne, which involve infestation of the sebaceous gland with *p. acnes*, as well as *Staphylococus aurus* or *Pseudomonas*. Various antibacterial agents have been utilized to treat acne, however, their efficacy is limited due to their low penetration into the hydrophobic environment of the sebaceous gland. The composition of the present invention, being hydrophobic by nature would facilitate an enhanced rate of penetration. Examples of useful antiacne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4, 4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate and cholate.

The intrinsic antibacterial and antiinflammatory effects of the solidifying agents, i.e., fatty alcohols and acids, of the composition of the present invention provide a combined synergetic effect that results in a better therapeutic response to treatment.

Eye infections are another preferred target for the composition of the present invention. Conjunctivitis, involving bacteria such as *Staphylococcus aureus, Streptococcus pneumoniae*, and *Haemophilus influenzae* is generally treated with antibiotic ointments, e.g., bacitracin 500 U/g or 0.3 percent ophthalmic ointment instilled into the affected eye. Yet, ointment applied into the eye created a sticky feeling and causes major disturbances to the patient. The composition of the present invention, which turns from semi-solid consistency into liquid instantly after application, does not have that disadvantage and thus, treatment compliance is expected to improve. The same advantage is expected when the composition of the present invention is topically applied to mucosal membranes, the oral cavity, the vagina or the rectum.

Another example is parachlorometaxylenol, which is an antimicrobial agent and is suitable for use in the compositions described in the present invention.

Phenols, in concentrations of about 0.2, 1.0, and 1.3 percent by weight are bacteriostatic, bactericidal, and fungicidal, respectively. While it is not intended that the present invention be bound by any particular theory, it is believed that the germicidal action of phenols at these concentrations is effected through protein denaturation. The phenol-protein interaction is relatively weak, allowing the phenol molecule to penetrate deeply into the tissue. Thus, phenol can penetrate relatively dense, intact keratinous matrices, such as the stratum corneum or the nail plate. Several phenol derivatives are more potent than phenol itself, and the most important among these are the halogenated phenols and bis-phenols, the alkyl-substituted phenols and the resorcinols.

Optionally, the present invention may provide a solution for body odors by including hydrophobic antibacterial compounds to help destroy and/or control the amount of bacteria present on the skin, which aids in body odor control.

Hydrophobic antibacterials useful in the present invention include triclosan, triclocarbon, eucalyptol, menthol, methylsalicylate, thymol, and mixtures thereof. Preferred are triclosan and triclocarbon. When included in the composition of the present invention, the hydrophobic antibacterials may be at a level of from about 0.1 percent to about 1.5 percent and preferably from about 0.1 percent to about 0.3 percent, by weight of the composition.

Antifungal Agents:

Fungal infections are another object of treatment using the compositions of the present invention. Superficial fungal infection of the skin is one of the commonest skin disease seen in general practice. Dermatophytosis is probably the most common superficial fungal infection of the skin. It is caused by a group of fungi, which are capable of metabolizing the keratin of human epidermis, nails or hair. There are 3 genera of dermatophytes causing dermatophytosis i.e., microsporum, trichophyton and epidermophyton.

Candidiasis is an infection caused by the yeast like fungus *Candida albicans* or occasionally other species of *Candida*. Clinical syndromes of candidiasis include (a) oral candidiasis (oral thrush); (b) candidiasis of the skin and genital mucous membrane; and (c) candida paronychia, which inflicts the nail.

The pharmaceutical composition of the present invention can contain an antifungal drug, which is active against dermatophytes and candida. The drug may include azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration. U.S. Pat. No. 4,352,808 discloses 3-aralkyloxy-2,3-dihydro-2-(1H-imidazolylmethyl)benzo[b]thiophene compounds having antifungal and antibacterial activity.

Steroidal Antiinflammatory Agents:

Suitable steroidal antiinflammatory agents usable in the composition of the present invention may include, although are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chloroprednisone, chloroprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof may be used. The preferred steroidal antiinflammatory for use in the present invention is hydrocortisone.

Table 2 below provides a summary of currently available corticosteroid agent.

TABLE 2

List of steroidal antiinflammatory agents for topical application

| Potency | Compound | Formulation |
|---|---|---|
| Very high | Clobetasol proprionate | Cream or ointment 0.05 percent |
| high | Halobetasol proprionate | Cream or ointment 0.05 percent |
| High | Betamethasone diproprionate | Cream or ointment 0.05 percent |
|  | Betamethasone valerate | Ointment 0.1 percent |
|  | Fluocinolone acetonide | Cream 0.02 percent |
|  | Halcinonide | Cream or ointment 0.1 percent |
| Medium | Betamethasone valerate | Cream 0.1 percent |
|  | Fluocinolone acetonide | Cream or ointment 0.020 percent |
|  | Hydrocortisone valerate | Cream or ointment 0.2 percent |
|  | Triamcinolone acetonide | Cream, ointment, or lotion 0.1 percent or 0.020 percent |
| Low | Hydrocortisone | Cream, ointment, or lotion 2.5 percent or 1.0 percent |

Since all corticosteroid drugs are hydrophobic, the carrier of the present invention is most suitable as a vehicle to facilitate an enhanced rate of penetration and better topical distribution thereof.

Furthermore, the intrinsic antiviral, antibacterial and antiinflammatory effects of the solidifying agents, i.e., fatty alcohols and acids, provide a combined synergetic effect that should result in a better therapeutic response to treatment.

Psoriasis is a very common chronic inflammatory skin disease, which may be the target of treatment using a composition of the present invention. Psoriasis is marked by periodic flare-ups of sharply defined red patches covered by a silvery, flaky surface.

Corticosteroid ointments, greasy preparations containing small amount of water, are commonly used for treating psoriasis. Their main disadvantage is in their stickiness, which remains for long time after treatment is over. In this respect it should be noted that the present invention exemplifies the use of a hydrocortisone containing composition that was prepared according to the teachings of the present invention (see Example 1 below). The hydrocortisone preparation was compared to a commercial composition (Example 2) and was shown be highly efficient in the treatment of psoriatic patients. Major reduction in the severity of the disease symptoms, i.e., disappearance of the silvery scales, and reduction of the oedema, erythema and pruritus were observed. Moreover the patients reported that unlike the ointments which are currently available in the market (see Table 2 above), the composition of the present invention was well distributed and absorbed into the skin, without leaving an undesirable greasiness and shiny appearance which characterized the prior art formulations.

Examples of other inflammatory diseases or disorders, which can be treated by the composition of the present invention, wherein the drug is a steroid are: seborrheic dermatitis of the face and trunk, seborrheic blepharitis, contact dermatitis, stasis dermatitis (gravitational eczema; varicose eczema), exfoliative dermatitis (erythroderma), lichen simplex chronicus, pemphigus, conjunctivitis and uveitis.

Topical antihistaminic preparations currently available include 1 percent and 2 percent diphenhydramine (Benadryl® and Caladryl®), 5 percent doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines can also be included in the composition of the present invention.

Additionally, so-called "natural" antiinflammatory agents are useful in context of the present invention. For example, candelilla wax, alpha bisabolol, aloe vera, Manjistha (extracted from plants in the genus Rubia, particularly Rubia cordifolia), and Guggal (extracted from plants in the genus Commiphora, particularly Commiphora mukul, may be used as an active ingredient in the composition of the present invention.

Non-Steroidal Antiinflammatory Drugs (NSAIDs):

Another preferred embodiment of the present invention is administration of non-steroidal antiinflammatory drugs (herein NSAIDs) using a composition of the present invention. NSAIDs have been used extensively in recent years for treatment of chronic rheumatic or arthritic conditions and for management of pain. The compounds are believed to bring relief by inhibiting biosynthesis of prostaglandins at affected joints or in other tissue areas. Salicylic acid, or aspirin, and ibuprofen are well-known examples of NSAIDs drugs. Patients using NSAIDs drugs administered orally face an increased risk for peptic ulcers and gastrointestinal blood loss resulting in anemia. Such adverse reactions especially plague patients taking NSAIDs drugs over prolonged periods. Administration of NSAIDs to using the carrier of the present invention will prevent gastrointestinal complications associated with the oral administration of NSAIDs. Such compositions can be used for prolonged treatment of arthritis and other diseases or disorders treated by NSAIDs drugs, while avoiding the gastrointestinal complications associated with oral dose delivery. Application of NSAIDs drugs in a topical composition to the skin of a patient allows a predetermined amount of the NSAIDs drug to be administered continuously to the patient and avoids undesirable effects present with a single or multiple administrations of larger dosages. By maintaining a sustained dosage rate, the NSAIDs drug level in the patient's blood can be better maintained within the optimal therapeutic range.

Examples of NSAIDs include the following categories: propionic acid derivatives; acetic acid derivatives; fenamic acid derivatives; biphenylcarboxylic acid derivatives; and oxicams. All of these NSAIDs are fully described in the U.S. Pat. No. 4,985,459 to Sunshine et al. which is incorporated herein by reference. Examples of useful NSAIDs include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen and bucloxic acid.

Antioxidants/Radical Scavengers:

Suitable antioxidants/radical scavengers useful in context of the present invention include ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used, as well as EDTA, BHT and the like.

Antibiotics:

Antibiotics which may be used in context of the composition of the present invention, include, but are not limited to, chloramphenicol, tetracyclines, synthetic and semi-synthetic penicillins, beta-lactames, quinolones, fluoroquinolones, macrolide antibiotics, peptide antibiotics, cyclosporines, erythromycin and clindamycin.

Topical Anesthetics:

Examples of topical anesthetic drugs useful in context of the composition of the present invention include benzocaine, lidocaine, bupivacaine, chloroprocaine, dibucaine, etidocaine, mepivacaine, tetracaine, dyclonine, hexylcaine, procaine, cocaine, ketamine, pramoxine, phenol, and pharmaceutically acceptable salts thereof.

Retinol:

Another preferred group of drugs useful in context of the composition of the present invention include retinol, all trans retinoic acid and derivatives, isomers and analogs thereof, collectively termed "retinoids". Compositions according to the present invention, which contain retinoids as the active ingredient can be used for the treatment of acne, seborrhea, various dermatoses, inflammation of the skin, mucosal membranes, eye, vagina and the rectum, psoriasis and cancers, by application onto the affected area.

Other Drugs:

As is further detailed hereinunder, it is possible to provide the composition of the present invention onto a dermal patch to generate a transdermal delivery apparatus and applying such patch onto the skin in order to attain effective superficial treatment or enhanced penetration of a drug into the skin or through the skin.

Utilizing such a strategy, one can apply drugs which are currently administered systemically or that require transdermal delivery, in the preferred therapeutic system of the present invention. The following provides some examples for such drugs.

A broad range of analgesics may be utilized including, without limitation, morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine.

A typical narcotic antagonist is haloxone. Exemplary antitussive agents include, without limitation, diphenhydramine, guaifenesin, hydromorphone, ephedrine, phenylpropanolamine, theophylline, codeine, noscapine, levopropoxyphene, carbetapentane, chlorpehndianol and benzonatate.

Among the sedatives which may be utilized are, without limitation, chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs are, without limitation, quinidine, propranolol, nifedipine, procaine, dobutamine, digitoxin, phenyloin, sodium nitroprusside, nitroglycerin, verapamil HCl, digoxin, nicardipine HCl, and isosorbide dinitrate.

Antiemetics are illustrated by, without limitation, thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include, without limitation, thyroxine, growth hormone (GH), interstitial cell stimulating hormone (ICSH), follicle-stimulating hormone (FSH), thyrotrophic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, the invention is applicable only to those hormones which have molecular weights and stereo configurations which will allow passage through the skin.

Female sex hormones which can be used include, without limitations, estradiol, diethylstilbestrol, conjugated estrogens, estrone, norethindrone, medroxyprogesterone, progesterone, and norgestrel.

Typical male sex hormones which may be utilized may be represented by, without limitation, testosterone, methyltestosterone, and fluoxymesterone.

The above listed active permeants may, along with others not specifically disclosed, be used separately or in combination according to the treatment regimen desired.

Cosmetic Agents:

The carrier according to the present invention can also be used to prepare cosmetics for beauty purpose by the addition of skin care agents and perfumes.

Sun Screen Agents:

Also useful in context of the composition of the present invention are sun screening agents. A wide variety of sun screening agents are described in U.S. Pat. No. 5,087,445, to Haffey et al. U.S. Pat. No. 5,073,372, to Turner et al., U.S. Pat. No. 5,073,371, to Turner et al. and Segarin, et al., at Chapter VIII, pages 189 et seq., of Cosmetics Science and Technology all of which are incorporated herein by reference in their entirety. Preferred among those sunscreens which are useful in the composition of the instant invention are those selected from the group consisting of 2-ethylhexyl p-methoxycinnamate, octyl methoxycinnamate, 1-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. Nos. 4,937,370, to Sabatelli and 4,999,186, to Sabatelli et al. These two later references are incorporated by reference herein in their entirety. The sun screening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sun screening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl) methylaminobenzoic acid ester of 2,4-hydroxybenzophenone, 4-N,N-(2-ethylhexyl)methylaminobenzoic acid ester with 4-hydroxydibenzoylmethane, 4-N,N-(2-ethylhexyl)methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Generally, the sunscreens can comprise from about 0.5 percent to about 20 percent of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206-38269, Aug. 25, 1978.

Artificial Tanning Agents and Accelerators:

Examples of artificial tanning agents accelerators which can be used in context of the present invention include dihydroxyacetone, tyrosine, tyrosine esters such as ethyl tyrosinate, and phospho-DOPA.

Reducing Body Odors:

The body fluids includes eccrine sweat, apocrine sweat, sebum, build up of sensible moisture from transepidermal water loss, vaginal discharge, urine, and mixtures thereof. The body odor are odors, which are generated as a result of the natural functioning of a human body. Such odors include, but are not limited to odors produced by microorganisms of the human skin (i.e. bacterial decomposition of skin secretions), urine, or vaginal discharge, and mixtures thereof. The present invention is therefore relevant to a method of reducing body odor comprising the application of a perfume-free, odor-absorbing composition which includes the carrier of the present invention.

Antiwrinkle and Antiskin Atrophy Agents:

Examples of antiwrinkle and antiskin atrophy actives which can be used in context of the present invention include retinoic acid and its derivatives (e.g., cis and trans); salicylic acid and derivatives thereof, sulfur-containing D and L amino acids and their derivatives and salts, particularly the N-acetyl derivatives, a preferred example of which is N-acetyl L-gsteine; thiols, e.g. ethane thiol; alpha-hydroxy acids, e.g. glycolic acid, and lactic acid; phytic acid, lipoic acid; lysophosphatidic acid, and skin peel agents (e.g., phenol and the like).

Excipients and Additional Agents:

The pharmaceutical or cosmetic composition of the present invention may further include a variety of pharmaceutical or cosmetic ingredients, which are added in order to fine-tune the consistency of the formulation, protect the formulation components from degradation and oxidation and bestow their cosmetic acceptability. Such excipients, may be selected from the group consisting of water, surfactants, emulsifiers, diglycerides, triglycerides, stabilizing agents, antioxidants, glycerol, ethanol, propanol, isopropanol, butanol, polymeric gelling agents, flavoring, colorant and odorant agents and other formulation components, used in the art of pharmaceutical and cosmetic formulary.

Additional active and inactive ingredients may also include, without limitation, local analgesics such as benzocaine, menthol, and the like (wherein menthol is also capable of providing a soothing, cooling sensation), as well emollients, antihistamines, fragrances, thickeners and preservatives other than those already listed.

Emollients:

The compositions of the present invention can also include an emollient. Emollient is used to smooth the surface of the skin. Examples of suitable emollients include, but are not limited to, volatile and non-volatile silicone oils (e.g., dimethicone, cyclomethicone, dimethiconol, and the like), highly branched hydrocarbons, and mixtures thereof. Emollients useful in the instant invention are further described in U.S. Pat. No. 4,919,934, to Deckner et al., which is incorporated herein by reference in its entirety. The emollients can typically comprise in total from about 0.1 percent to about 25 percent, more preferably from about 0.5 percent to about 10 percent, and most preferably from about 0.5 percent to about 5 percent by weight of the composition.

A variety of additional ingredients can be incorporated into the composition of the present invention. Non-limiting examples of these additional ingredients include vitamins and derivatives thereof (e.g. tocopherol, panthenol, and the like); other thickening agents (e.g., polyacrylamide and $C_{13}$-$C_{14}$ isoparaffin and laureth-7, available as Sepigel 305 from Seppic Corp., Fairfield, N.J.; and branched polysaccharides such as scleroglucan available under the tradename Clearogel® CS 11 from Michel Mercier Products Inc., Mountainside, N.J.); saturated and/or unsaturated alkyl alpha hydroxy acids; resins; gums (e.g. guar gum, xanthan gum and the like); waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220®); abrasive scrub particles for cleansing and exfoliating the skin, e.g., ACuscrub® Mild Abrasives (e.g., ACuscrub® 30, 31, 32, 40, 41, 42, 43, 44, 50, 51, and 52) available from Allied Signal, Inc., Morristown, N.J.; and 3M Brand PMU Capsules microencapsulated mineral oil available from 3M Corporation, St. Paul, Minn.; preservatives for maintaining the antimicrobial integrity of the compositions; skin penetration aids such as DMSO, 1-dodecylazacycloheptan-2-one (available as Azone® from the Upjohn Co.) and the like; skin bleaching (or lightening) agents including but not limited to hydroquinone, kojic acid and sodium metabisulfite; chelators and sequestrants; and aesthetic components such as fragrances, pigments, colorings, essential oils, skin sensates, astringents, skin soothing agents, skin healing agents and the like, non-limiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

The carrier system may also comprise, when desired, a suitable gelling agent including, but not limited to, cellulose esters such as hydroxypropyl cellulose (Klucel®), hydroxyethyl cellulose (Natrosol®), polyvinylpyrrolidone (Povidone®), carboxyvinyl polymer (HIVIS105®) and the like that may be provided in any amount necessary to thicken the composition to a desired gel consistency. When formulated as a gel, the base composition exhibits favorable spreadability characteristics. In addition, it remains visible on the skin surface longer, thereby instilling in the user the impression that the vehicle is more completely delivering its active ingredient(s).

In addition to the aforementioned ingredients, it should also be noted that the following ingredients may also be included in the inventive composition, as desired: coloring agents, fragrances, conditioners, moisturizers, surfactants, antioxidants, preservatives, etc.

Preferred ingredients are saturated and/or unsaturated alkyl alpha hydroxy acids, at a level of from about 0.05 percent to about 5 percent by weight of the composition, such as lactic acid, lactate salts (e.g., ammonium and quaternary alyl ammonium), glycolic acid, glycolate salts (e.g., ammonium and quaternary allyl ammonium), and fruit acids. A discussion of alpha hydroxy acids is disclosed in Walter P. Smith, Hydroxy Acids and Skin Aging, Soap/Cosmetics/Chemical Specialties. pp. 54-59, (September 1993), which is herein incorporated by reference in its entirety.

Preservatives:

Antimicrobial preservatives useful in the present invention include biocidal and biostatic compounds (substances that kill microorganisms and/or regulate the growth of microorganisms). Suitable antimicrobial preservatives have a solubility of 0.3 percent or greater. In addition, suitable preservatives are those which can come into contact with skin without high irritation potential. Preservatives suitable for use in the present compositions are described in U.S. Pat. No. 5,534,165, to Pilosof et al.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Colorants and Dyes:

Colorants and dyes can be optionally added to the odor absorbing compositions for visual appeal and performance impression. When colorants are used, care must be taken in the selection of choosing dyes that will not color skin. Preferred colorants for use in the present compositions are highly water-soluble dyes, e.g., acid blue 3, acid blue 104, acid green 1, acid green 25, acid yellow 3, acid yellow 73 sodium salt, D&C green No. 5, 6 & 8, D&C yellow No. 7, 8, 10 & 11, D&C violet No. 2, FD&C blue No. 1 & 2, FD&C green No. 3, FD&C yellow No. 5 & 6, and mixtures thereof.

Other Optional Ingredients:

The composition of the present invention can optionally contain adjunct odor-controlling materials, such as zinc salts, cationic polymers, anionic polymers, carbonate salts, bicarbonate salts, zeolites, and activated carbon; chelating agents; colorants; and/or antiperspirants.

Optionally, the composition of the present invention can include zinc salts for added odor absorption and/or antimicrobial benefit for the cyclodextrin solution. Zinc compounds have been used most often for their ability to ameliorate malodor, e.g., in mouth wash products, as disclosed in U.S. Pat. Nos. 4,325,939 and 4,469,674 to Shah, et al. Highly-ionized zinc salts, such as zinc chloride, provide the best source of zinc ions. The zinc salt, zinc phenolsulfonate, is preferred for use in the skin composition of the present invention; although others may also fall within the scope of the present invention. However, care must be taken in selecting zinc salts, as well as their levels, since some may be irritants to the skin and they are not preferred for use in the present invention.

Administration Via Dermal Patch:

The compositions of the present invention may also be delivered to the skin using conventional dermal-type patches or articles, wherein the active ingredients composition is contained within a laminated structure, that serves as a drug delivery device to be affixed to the skin. In such a structure, the active ingredients composition is contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredients and to any other components of the active ingredients-containing composition, thus preventing loss of any components through the upper surface of the device. The backing layer may be either occlusive or nonocclusive, depending on whether it is desired that the skin become hydrated during active ingredients delivery. The backing is preferably made of a sheet or film of a preferably flexible elastomeric material. Examples of polymers that are suitable for the backing layer include polyethylene, polypropylene, and polyesters.

During storage and prior to use, the laminated structure includes a release liner. Immediately prior to use, this layer is removed from the device to expose the basal surface thereof, either the active ingredients reservoir or a separate contact adhesive layer, so that the system may be affixed to the skin. The release liner should be made from a active ingredients/vehicle impermeable material.

Such devices may be fabricated using conventional techniques, known in the art, for example by casting a fluid admixture of adhesive, active ingredients and vehicle onto the backing layer, followed by lamination of the release liner. Similarly, the adhesive mixture may be cast onto the release liner, followed by lamination of the backing layer. Alternatively, the active ingredients reservoir may be prepared in the absence of active ingredients or excipient, and then loaded by "soaking" in a active ingredients/vehicle mixture.

Therapeutic Effect and Dosage:

The therapeutic efficacy of the compositions described herein can be determined by standard pharmaceutical procedures in experimental animal models or human beings. The data obtained from these studies can be used in formulating a range of dosage for use in human (See e.g., Fingl, et al., 1975, in "The Pharmacological Basis of Therapeutics", Ch. 1 p. 1).

The effective concentration of the drug is calculated by procedures known in the art that can be employed to determine the effective local concentration. For example, corticosteroid induced vasoconstriction in man may provide a preliminary useful hint to topical antiinflammatory activity.

The amount of a composition to be administered will, of course, be dependent on the subject being treated, the severity of the affliction, the manner of administration, the judgment of the prescribing physician, etc.

Short term studies over one or two weeks may not be the only relevant investigation for the clinical comparison of the topical drugs. In practice these are sometimes applied over long periods of time and the differences may be apparent only after months of treatment. For this reason, depending on the novelty of the product and the indications claimed, certain studies of efficacy as well as of safety will be required.

Since the hydrophobic agent can be derived from a biological source, it is necessary to assess the repeatability of the therapeutic effect as well as the reproducibility, the specificity and the accuracy of the agent. This should be done by an analytical chemistry laboratory which is defined as GLP (Good Laboratory Practice).

Compositions of the present invention may, if desired, be presented in a bottle or jar or other container approved by the FDA, which may contain one or more unit dosage forms containing the active ingredient. Compositions such as those described in the present invention may be particularly susceptible to microbial and other contamination, and special measures need to be taken to prevent any contamination. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition. Suitable conditions indicated on the label may include treatment for acne or for psoriasis and the like.

The gist and advantages of the present invention over the prior art:

The gist of the present invention is based on the striking discovery that the addition of fatty alcohols to hydrophobic liquids, such as saturated, mono-unsaturated or poly-unsaturated oils, as well as mineral and silicone oils, may alter the physicochemical properties of the material, including the solidification thereof. This appears to be particularly relevant when the fatty alcohol has a molecular weight greater than 200 Da and at least one hydroxyl group in its chemical structure. The addition of a fatty alcohol to a liquid oil also gives rise to thixotropic properties (e.g., being semi-solid at rest and liquid upon application of shear forces thereto). This property enables application of a thixotropic mixture as a semi-solid state to a body surface, which subsequently becomes substantially liquid and therefore more spreadable and penetrable when rubbed onto the body surface. Thus, one of the most important properties of the carrier and composition of the present invention is that they are semi-solid at rest and that they liquefy upon application of shear forces thereto. Semi-solid hydrophobic formulations are important not only for the pharmaceutical market but also for cosmetic products, such as carriers of sunscreen compounds, oil-soluble plant extracts, materials for scrubbing purposes and other active and non-active cosmetic ingredients. Unlike aqueous liquids, which are rather easy to solidify due to their hydrogen bond forming ability, oils are difficult to solidify. Several methods have been proposed to increase the viscosity of oils. Various gelling agent, such as inorganic complexing agents (U.S. Pat. No. 4,780,309), hydrocolloids (U.S. Pat. No. 4,576,645), polymers and copolymers (U.S. Pat. Nos. 5,985,821; 5,925, 707), polysaccharides (U.S. Pat. No. 5,961,998) have been previously described in the context of solidifying oils for use in food and cosmetics. The use of waxes, fatty alcohols, fatty acids and 12 hydroxy stearic acid in solidifying waste oils, in order to facilitate the removal of such oils have also been described (JP-A-112385/1979; JP-A-106298/1980). U.S. Pat. No. 5,817,322 teaches pharmaceutical compositions, comprising an oil and beeswax as a gelling agent, which form a netted framework of the beeswax and form a film after application on a body surface.

However, the prior art fails to teach a carrier or composition for topical application which is semi-solid at rest and which liquefies upon application of shear forces thereto.

EXAMPLES

Additional objects, advantages, and novel features of the present invention will become apparent to one ordinarily skilled in the art upon examination of the following examples, which are not intended to be limiting. Additionally, the various embodiments and aspects of the present invention as delineated hereinabove and as claimed in the claims section below finds experimental support in the following examples.

Example 1

Preparation of a Corticosteroid Composition

Stearyl alcohol (60 grams) was heated to 80° C. USP olive oil (940 grams) was heated to the same temperature. While at 80° C., the stearyl alcohol was added to the preheated olive oil. 20 grams glycerin, 20 grams tri-stearin, 1 gram of an antioxidant mixture were added by agitation. 1 gram of betamethasone valerate was added and the mixture was poured into containers (5 gram tubes) and was allowed to cool spontaneously. While the mixture cooled to ambient temperature it gradually turned into a semi-solid.

Example 2

Efficacy of the Corticosteroid Composition for the Treatment of Psoriasis

In a preliminary experiment, five patients with psoriasis were treated with the corticosteroid preparation described in Example 1, twice a day, for 10 days. In three out of five patients the psoriatic plaques and skin thickness were significantly reduced after 7-10 days of treatment (FIG. 1). The forth patient had a moderate improvement and fifth showed only mild response to the treatment.

Example 3

A Double Blind Comparative Study Between the Corticosteroid Composition and a Conventional Ointment Eight subjects were requested to apply 1 gram of the corticosteroid composition described in Example 1 on one arm and 1 gram of commercial betamethasone valerate ointment, on the other arm. The study was performed in a double blind manner. The subjects had to describe their opinion about the ease of application, ease of spreading, spreadability and penetrability of each of the products and to give their scores on a scale of 0 to 3 (0=poor; 1=barely acceptable; 2=acceptable and 3=excellent).

As can be clearly seen in Table 3 below, the corticosteroid composition of Example 1 obtained higher score in each of the study parameters.

TABLE 3

Comparison between the corticosteroid composition and Betamethasone commercial ointment

| Parameters | Corticosteroid Composition (Example 1) mean Score | Commercial Betamethasone valerate ointment mean Score |
| --- | --- | --- |
| Ease of application | 2.5 | 1.8 |
| Ease of spreading | 2.4 | 1.8 |
| Spreadability | 2.8 | 1.6 |
| Penetrability | 2.4 | 2.0 |
| Lack of stickiness | 2.6 | 1.0 |
| Lack of greasiness | 2.6 | 0.8 |

TABLE 3-continued

Comparison between the corticosteroid composition and Betamethasone commercial ointment

| Parameters | Corticosteroid Composition (Example 1) mean Score | Commercial Betamethasone valerate ointment mean Score |
|---|---|---|
| Lack of shiny look | 1.9 | 1.4 |
| Overall rating | 2.6 | 1.6 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An oleaginous pharmaceutical carrier comprising:
a mixture comprising, by weight:
75-99 percent of a hydrophobic solvent, and
1-25 percent of a solidifying agent, wherein said solidifying agent is selected from the group consisting of (i) at least one long chain fatty alcohol having at least 15 carbon atoms in its carbon backbone (ii) at least one fatty acid having at least 18 carbons in its carbon backbone, and (iii) a mixture thereof
wherein the pharmaceutical carrier is semi-solid at rest and liquefies upon application of shear forces thereto; and
wherein the carrier is free of a netted framework of solidifying agent.

2. A pharmaceutical composition, comprising the carrier of claim 1, further comprising a therapeutically effective amount of a biologically active substance.

3. The pharmaceutical composition of claim 2, wherein the biologically active substance is selected from the group of consisting of an antibiotic agent, a free radical generating agent, an antifungal agent, an antiviral agent, a non-steroidal anti-inflammatory drug, an immunosuppressant, an antihistamine agent, an anti-inflammatory agent, a retinoid agent, a tar agent, an antipruritics agent and a scabicide agent.

4. The pharmaceutical composition of claim 3, wherein the antibiotic agent comprises a tetracycline antibiotic.

5. The pharmaceutical composition of claim 2, wherein said hydrophobic solvent includes an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojoba oil.

6. The pharmaceutical composition of claim 2, wherein said hydrophobic solvent includes an oil selected from the group consisting of marine animal derived oils, terrestrial animal derived oils, mineral oils, silicone oils and plant-derived oils.

7. The pharmaceutical composition of claim 2, wherein said hydrophobic solvent includes an oil selected from the group consisting of omega-3 oil and omega-6 oil.

8. The pharmaceutical composition of claim 2, wherein the hydrophobic solvent comprises a silicone oil.

9. The pharmaceutical composition of claim 2, wherein the carrier provides a protective moisture barrier.

10. The pharmaceutical composition of claim 2, wherein the composition spreads easily and is non sticky.

11. The pharmaceutical composition of claim 2, wherein said solidifying agent includes a 12-hydroxy fatty acid and or behenyl alcohol.

12. The pharmaceutical composition of claim 2,
wherein the solidifying agent is solid at ambient temperature; and
wherein the biologically active substance comprises a tetracycline antibiotic in a therapeutically effective amount to treat a disease or disorder of the skin or mucosal membrane.

13. A method of applying:
a pharmaceutical composition to a skin or a mucosal membrane having a disease or disorder, comprising topically administering the pharmaceutical composition to the skin or the mucosal membrane surface, said pharmaceutical composition comprising, by weight, a mixture of:
75-99 percent of a hydrophobic solvent,
1-25 percent of a solidifying agent, wherein said solidifying agent is selected from the group consisting of (i) at least one long chain fatty alcohol having at least 15 carbon atoms in its carbon backbone (ii) at least one fatty acid having at least 18 carbons in its carbon backbone and (iii) a mixture thereof; and
a biologically active agent,
wherein the composition is semi-solid at rest and liquefies upon application of shear forces thereto; and
wherein the composition is free of a netted framework of solidifying agent.

14. The method of claim 13, wherein on application the composition freely spreads on the skin surface or mucosal membrane and is rapidly absorbed.

15. The method of claim 14, wherein the composition spreads without film formation.

16. The method of claim 13, wherein the composition is adapted to facilitate enhanced penetration of the active agent.

17. The method of claim 13, wherein the disease or disorder is selected from the group consisting of psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis and exfoliative dermatitis.

18. The method of claim 13, wherein said biologically active substance is selected from the group of consisting of an antibiotic agent, a free radical generating agent, an antifungal agent, an antiviral agent, a non-steroidal anti-inflammatory drug, an immunosuppressant, an antihistamine agent, an anti-inflammatory agent, a retinoid agent, a tar agent, an antipruritic agent and a scabicide agent.

19. The method of claim 13, wherein the biologically active agent comprises a tetracycline antibiotic.

20. The method of claim 13, wherein said hydrophobic solvent includes an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojoba oil.

21. The method of claim 13, wherein said hydrophobic solvent includes an oil selected from the group consisting of marine animal derived oils, terrestrial animal derived oils, mineral oils, silicone oils and plant-derived oils.

22. The method of claim 13, wherein said hydrophobic solvent includes an oil selected from the group consisting of omega-3 oil and omega-6 oil.

23. The method of claim 13, wherein the composition provides a protective moisture barrier.

24. The method of claim 15, wherein the composition is delivered by means of a dermal patch or as a suppository.

25. The method of claim 13, wherein said solidifying agent includes a 12-hydroxy fatty acid and or behenyl alcohol.

26. The method of claim 13, wherein the solidifying agent is solid at ambient temperature;
wherein the biologically active substance comprises a tetracycline antibiotic in a therapeutically effective amount to treat a disease or disorder of the skin or mucosal membrane.

27. A method of preparing an oleaginous pharmaceutical carrier, the method comprising the steps of mixing a hydrophobic solvent and a solidifying agent at a temperature above a melting temperature of the solidifying agent so as to obtain a mixture containing 75-99 percent of the hydrophobic solvent by weight and 1-25 percent of the solidifying agent by weight; and cooling the mixture,
wherein said solidifying agent is selected from the group consisting of (i) at least one long chain fatty alcohol having at least 15 carbon atoms in its carbon backbone (ii) at least one fatty acid having at least 18 carbons in its carbon backbone, and (iii) a mixture thereof; and
wherein the pharmaceutical carrier is semi-solid at rest and liquefies upon application of shear forces thereto.

28. The method of claim 27, further comprising:
mixing into the mixture a therapeutically or cosmetically effective amount of a biologically active substance.

29. The method of claim 18, wherein the antibiotic agent is selected from the group consisting of chloramphenicol, a tetracyclines, a synthetic penicillins, a semi-synthetic penicillin, a beta-lactam, a quinolone, a fluoroquinolone, a macrolide antibiotic, a peptide antibiotic, a cyclosporine, erythromycin clyndamycin and mixtures thereof.

30. The pharmaceutical composition of claim 2, wherein the biologically active substance is selected from the group consisting of chloramphenicol, a tetracyclines, a synthetic penicillin, semi-synthetic penicillins, a beta-lactam, a quinolone, a fluoroquinolone, a macrolide antibiotic, a peptide antibiotic, a cyclosporine, erythromycin, clyndamycin and mixtures thereof.

31. A method of treating a disease or disorder of a skin or a mucosal membrane comprising:
topically administering a pharmaceutical composition to the skin or the mucosal membrane, said pharmaceutical composition comprising, by weight, a mixture of:
75-99 percent of a hydrophobic solvent,
1-25 percent of a solidifying agent, wherein said solidifying agent is selected from the group consisting of (i) at least one long chain fatty alcohol having at least 15 carbon atoms in its carbon backbone (ii) at least one fatty acid having at least 18 carbons in its carbon backbone and (iii) a mixture thereof; and
a biologically active agent selected from the group consisting of an antibiotic agent, a free radical generating agent, an antifungal agent, an antiviral agent, a non-steroidal anti-inflammatory drug, an immunosuppressant, an antihistamine agent, an anti-inflammatory agent, a retinoid agent, a tar agent, an antipruritics agent, and a scabicide agent and wherein the antibiotic agent is selected from the group consisting of chloramphenicol, tetracyclines, synthetic and semi-synthetic penicillins, beta-lactams, quinolones, fluoroquinolones, macrolide antibiotics, peptide antibiotics, cyclosporines, erythromycin, clyndamycin, and mixtures thereof;
wherein the composition is semi-solid at rest and liquefies upon application of shear forces thereto;
wherein the composition is free of a netted framework of solidifying agent; and
wherein the disease or disorder is selected from the group consisting of psoriasis, acne, seborrhea, seborrheic dermatitis, alopecia, excessive hair growth, ichthyosis, infection, inflammation, wounds, burns, cuts, ulcers, psoriasis, seborrheic dermatitis of the face and trunk, seborrheic blepharitis, contact dermatitis, stasis dermatitis, and exfoliative dermatitis.

* * * * *